United States Patent
Twomey

(10) Patent No.: US 10,383,649 B2
(45) Date of Patent: *Aug. 20, 2019

(54) TRIGGER LOCKOUT AND KICKBACK MECHANISM FOR SURGICAL INSTRUMENTS

(71) Applicant: COVIDIEN LP, Mansfield, MA (US)

(72) Inventor: John R. Twomey, Superior, CO (US)

(73) Assignee: COVIDIEN LP, Mansfield, MA (US)

(*) Notice: Subject to any disclaimer, the term of this patent is extended or adjusted under 35 U.S.C. 154(b) by 689 days.

This patent is subject to a terminal disclaimer.

(21) Appl. No.: 14/814,602

(22) Filed: Jul. 31, 2015

(65) Prior Publication Data

US 2015/0335341 A1 Nov. 26, 2015

Related U.S. Application Data

(63) Continuation of application No. 13/401,964, filed on Feb. 22, 2012, now Pat. No. 9,113,940, which is a (Continued)

(51) Int. Cl.
*A61B 17/29* (2006.01)
*A61B 18/14* (2006.01)
(Continued)

(52) U.S. Cl.
CPC ........ *A61B 17/2909* (2013.01); *A61B 17/295* (2013.01); *A61B 18/1445* (2013.01);
(Continued)

(58) Field of Classification Search
CPC ............ A61B 18/1442; A61B 18/1445; A61B 2018/1452; A61B 2018/1455;
(Continued)

(56) References Cited

U.S. PATENT DOCUMENTS

| 371,664 A | 10/1887 | Brannan et al. |
| 702,472 A | 6/1902 | Pignolet |

(Continued)

FOREIGN PATENT DOCUMENTS

| CA | 2104423 A1 | 2/1994 |
| CA | 2520413 A1 | 3/2007 |

(Continued)

OTHER PUBLICATIONS

US. Appl. No. 08/926,869, filed Sep. 10, 1997, James G. Chandler.
(Continued)

*Primary Examiner* — Katrina M Stransky
*Assistant Examiner* — Katherine H Schwiker

(57) ABSTRACT

A forceps includes an end effector assembly including first and second jaw members, a blade, a lever member operably coupled to the end effector, a trigger member operably coupled to the blade and defining an actuation path therealong. A trigger safety member is pivotably coupled to the lever member such that, when the lever member is disposed in an initial position, the trigger safety member is disposed in a position blocking the trigger member. When the lever member is disposed in a compressed position, the trigger safety member is disposed in a position, wherein the trigger safety member is displaced from the actuation path to permit movement of the trigger member, wherein the safety member rotates relative to the lever member as a function of movement of the lever member to block/unblock the trigger member.

20 Claims, 10 Drawing Sheets

Related U.S. Application Data continuation-in-part of application No. 13/006,538, filed on Feb. 3, 2015, now Pat. No. 8,945,175.

(51) Int. Cl.
  *A61B 17/295* (2006.01)
  *A61B 17/00* (2006.01)
  *A61B 18/00* (2006.01)

(52) U.S. Cl.
  CPC ............ *A61B 2017/00734* (2013.01); *A61B 2017/2946* (2013.01); *A61B 2018/0063* (2013.01); *A61B 2018/00589* (2013.01); *A61B 2018/00595* (2013.01); *A61B 2018/1455* (2013.01)

(58) Field of Classification Search
  CPC ...... A61B 2018/1457; A61B 2018/146; A61B 2018/1412; A61B 2018/1415; A61B 2018/00601; A61B 2018/00916; A61B 17/295; A61B 2017/32004; A61B 2017/2901; A61B 2017/2902; A61B 2017/2903; A61B 2017/2945; A61B 2017/2946; A61B 2017/2919; A61B 2017/292; A61B 2017/2922; A61B 2017/2923; A61B 2017/2924; A61B 2017/00367; A61B 2017/00371; A61B 6/102; A61B 6/105; A61B 17/2909; A61B 2017/291; A61B 2017/2912; A61B 2017/2913; A61B 2017/2917; A61B 2017/2918; A61B 2017/2925; A61B 2017/2947; A61B 2018/1432; A61B 2018/1861; A61B 2017/07285
  USPC .................. 227/178.1, 179.1, 175.2, 180.1
  See application file for complete search history.

(56) References Cited

U.S. PATENT DOCUMENTS

| | | | |
|---|---|---|---|
| 728,883 A | 5/1903 | Downes |
| 1,586,645 A | 6/1926 | Bierman |
| 1,813,902 A | 7/1931 | Bovie |
| 1,822,330 A | 9/1931 | Ainslie |
| 1,852,542 A | 4/1932 | Sovatkin |
| 1,908,201 A | 5/1933 | Welch et al. |
| 1,918,889 A | 7/1933 | Bacon |
| 2,002,594 A | 5/1935 | Wappler et al. |
| 2,011,169 A | 8/1935 | Wappler |
| 2,031,682 A | 2/1936 | Wappler et al. |
| 2,054,149 A | 9/1936 | Wappler |
| 2,113,246 A | 4/1938 | Wappler |
| 2,141,936 A | 12/1938 | Schmitt |
| 2,176,479 A | 10/1939 | Willis |
| 2,245,030 A | 6/1941 | Gottesfeld et al. |
| 2,279,753 A | 4/1942 | Knopp |
| 2,305,156 A | 12/1942 | Grubel |
| 2,327,353 A | 8/1943 | Karle |
| 2,632,661 A | 3/1953 | Cristofv |
| 2,668,538 A | 2/1954 | Baker |
| 2,796,065 A | 6/1957 | Kapp |
| 2,824,915 A | 2/1958 | Buturuga |
| 3,073,311 A | 1/1963 | Tibbs et al. |
| 3,100,489 A | 8/1963 | Bagley |
| 3,204,807 A | 9/1965 | Ramsing |
| 3,372,288 A | 3/1968 | Wigington |
| 3,459,187 A | 8/1969 | Pallotta |
| 3,561,448 A | 2/1971 | Peternel |
| 3,643,663 A | 2/1972 | Sutter |
| 3,648,001 A | 3/1972 | Anderson et al. |
| 3,651,811 A | 3/1972 | Hildebrandt et al. |
| 3,678,229 A | 7/1972 | Osika |
| 3,720,896 A | 3/1973 | Beierlein |
| 3,763,726 A | 10/1973 | Hildebrand |
| 3,779,918 A | 12/1973 | Ikeda et al. |
| 3,798,688 A | 3/1974 | Wasson |
| 3,801,766 A | 4/1974 | Morrison, Jr. |
| 3,839,614 A | 10/1974 | Saganowski et al. |
| 3,862,630 A | 1/1975 | Balamuth |
| 3,863,339 A | 2/1975 | Reaney et al. |
| 3,866,610 A | 2/1975 | Kletschka |
| 3,875,945 A | 4/1975 | Friedman |
| 3,897,786 A | 8/1975 | Garnett et al. |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 3,970,088 A | 7/1976 | Morrison |
| 3,987,795 A | 10/1976 | Morrison |
| 4,005,714 A | 2/1977 | Hiltebrandt |
| 4,016,881 A | 4/1977 | Rioux et al. |
| 4,031,898 A | 6/1977 | Hiltebrandt et al. |
| 4,041,952 A | 8/1977 | Morrison, Jr. et al. |
| 4,043,342 A | 8/1977 | Morrison, Jr. |
| 4,074,718 A | 2/1978 | Morrison, Jr. |
| 4,076,028 A | 2/1978 | Simmons |
| 4,080,820 A | 3/1978 | Allen |
| 4,088,134 A | 5/1978 | Mazzariello |
| 4,102,471 A | 7/1978 | Lore et al. |
| D249,549 S | 9/1978 | Pike |
| 4,112,950 A | 9/1978 | Pike |
| 4,127,222 A | 11/1978 | Adams |
| 4,128,099 A | 12/1978 | Bauer |
| 4,165,746 A | 8/1979 | Burgin |
| 4,187,420 A | 2/1980 | Piber |
| 4,200,104 A | 4/1980 | Harris |
| 4,200,105 A | 4/1980 | Gonser |
| 4,233,734 A | 11/1980 | Bies |
| 4,236,470 A | 12/1980 | Stenson |
| 4,274,413 A | 6/1981 | Hahn et al. |
| 4,300,564 A | 11/1981 | Furihata |
| 4,306,561 A | 12/1981 | de Medinaceli |
| 4,311,145 A | 1/1982 | Esty et al. |
| D263,020 S | 2/1982 | Rau, III |
| 4,315,510 A | 2/1982 | Kihn |
| 4,363,944 A | 12/1982 | Poirier |
| 4,370,980 A | 2/1983 | Lottick |
| 4,375,218 A | 3/1983 | DiGeronimo |
| 4,394,552 A | 7/1983 | Schlosser |
| 4,416,276 A | 11/1983 | Newton et al. |
| 4,418,692 A | 12/1983 | Guay |
| 4,443,935 A | 4/1984 | Zamba et al. |
| 4,452,246 A | 6/1984 | Bader et al. |
| 4,470,786 A | 9/1984 | Sano et al. |
| 4,492,231 A | 1/1985 | Auth |
| 4,493,320 A | 1/1985 | Treat |
| 4,503,855 A | 3/1985 | Maslanka |
| 4,506,669 A | 3/1985 | Blake, III |
| 4,509,518 A | 4/1985 | McGarry et al. |
| 4,513,271 A | 4/1985 | Reisem |
| 4,535,773 A | 8/1985 | Yoon |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,619,258 A | 10/1986 | Pool |
| 4,624,254 A | 11/1986 | McGarry et al. |
| 4,625,723 A | 12/1986 | Altnether et al. |
| 4,644,950 A | 2/1987 | Valli |
| 4,655,215 A | 4/1987 | Pike |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,674,499 A | 6/1987 | Pao |
| 4,685,459 A | 8/1987 | Koch et al. |
| 4,733,662 A | 3/1988 | DeSatnick et al. |
| D295,893 S | 5/1988 | Sharkany et al. |
| D295,894 S | 5/1988 | Sharkany et al. |
| 4,753,235 A | 6/1988 | Hasson |
| 4,754,892 A | 7/1988 | Retief |

(56) References Cited

U.S. PATENT DOCUMENTS

| | | |
|---|---|---|
| 4,763,669 A | 8/1988 | Jaeger |
| D298,353 S | 11/1988 | Manno |
| 4,781,175 A | 11/1988 | McGreevy et al. |
| D299,413 S | 1/1989 | DeCarolis |
| 4,805,616 A | 2/1989 | Pao |
| 4,827,927 A | 5/1989 | Newton |
| 4,827,929 A | 5/1989 | Hodge |
| 4,829,313 A | 5/1989 | Taggart |
| 4,846,171 A | 7/1989 | Kauphusman et al. |
| 4,887,612 A | 12/1989 | Esser et al. |
| 4,890,610 A | 1/1990 | Kirwan, Sr. et al. |
| 4,938,761 A | 7/1990 | Ensslin |
| 4,947,009 A | 8/1990 | Osika et al. |
| 4,973,801 A | 11/1990 | Frick et al. |
| 4,985,030 A | 1/1991 | Melzer et al. |
| 5,007,908 A | 4/1991 | Rydell |
| 5,019,678 A | 5/1991 | Templeton et al. |
| 5,026,370 A | 6/1991 | Lottick |
| 5,026,371 A | 6/1991 | Rydell et al. |
| 5,035,695 A | 7/1991 | Weber, Jr. et al. |
| 5,037,433 A | 8/1991 | Wilk et al. |
| 5,042,707 A | 8/1991 | Taheri |
| 5,047,046 A | 9/1991 | Bodoia |
| 5,052,402 A | 10/1991 | Bencini et al. |
| 5,078,716 A | 1/1992 | Doll |
| 5,084,057 A | 1/1992 | Green et al. |
| 5,085,659 A | 2/1992 | Rydell |
| 5,099,840 A | 3/1992 | Goble et al. |
| 5,100,430 A | 3/1992 | Avellanet et al. |
| 5,108,392 A | 4/1992 | Spingler |
| 5,112,343 A | 5/1992 | Thornton |
| 5,116,332 A | 5/1992 | Lottick |
| 5,122,139 A | 6/1992 | Sutter |
| 5,144,323 A | 9/1992 | Yonkers |
| 5,147,357 A | 9/1992 | Rose et al. |
| 5,151,102 A | 9/1992 | Kamiyama et al. |
| 5,151,978 A | 9/1992 | Bronikowski et al. |
| 5,158,561 A | 10/1992 | Rydell et al. |
| 5,169,396 A | 12/1992 | Dowlatshahi et al. |
| 5,176,695 A | 1/1993 | Dulebohn |
| 5,190,541 A | 3/1993 | Abele et al. |
| 5,196,009 A | 3/1993 | Kirwan, Jr. |
| 5,197,964 A | 3/1993 | Parins |
| 5,209,747 A | 5/1993 | Knoepfler |
| 5,211,655 A | 5/1993 | Hasson |
| 5,215,101 A | 6/1993 | Jacobs et al. |
| 5,217,457 A | 6/1993 | Delahuerga et al. |
| 5,217,458 A | 6/1993 | Parins |
| 5,217,460 A | 6/1993 | Knoepfler |
| 5,219,354 A | 6/1993 | Choudhury et al. |
| 5,231,997 A | 8/1993 | Kikuchi et al. |
| 5,244,462 A | 9/1993 | Delahuerga et al. |
| 5,250,047 A | 10/1993 | Rydell |
| 5,250,056 A | 10/1993 | Hasson |
| 5,250,063 A | 10/1993 | Abidin et al. |
| 5,254,129 A | 10/1993 | Alexander |
| 5,258,001 A | 11/1993 | Corman |
| 5,258,006 A | 11/1993 | Rydell et al. |
| 5,261,918 A | 11/1993 | Phillips et al. |
| 5,267,998 A | 12/1993 | Hagen |
| 5,269,780 A | 12/1993 | Roos |
| 5,269,804 A | 12/1993 | Bales et al. |
| D343,453 S | 1/1994 | Noda |
| 5,275,615 A | 1/1994 | Rose |
| 5,277,201 A | 1/1994 | Stern |
| 5,281,220 A | 1/1994 | Blake, III |
| 5,282,799 A | 2/1994 | Rydell |
| 5,282,800 A | 2/1994 | Foshee et al. |
| 5,282,826 A | 2/1994 | Quadri |
| 5,290,286 A | 3/1994 | Parins |
| 5,290,287 A | 3/1994 | Boebel et al. |
| 5,300,082 A | 4/1994 | Sharpe et al. |
| 5,304,203 A | 4/1994 | El-Mallawany et al. |
| 5,308,353 A | 5/1994 | Beurrier |
| 5,308,357 A | 5/1994 | Lichtman |
| 5,312,433 A | 5/1994 | Boebel et al. |
| 5,313,027 A | 5/1994 | Inoue et al. |
| 5,314,445 A | 5/1994 | Heidmueller nee Degwitz et al. |
| 5,314,463 A | 5/1994 | Camps et al. |
| 5,318,589 A | 6/1994 | Lichtman |
| 5,324,289 A | 6/1994 | Eggers |
| D348,930 S | 7/1994 | Olson |
| 5,326,806 A | 7/1994 | Yokoshima et al. |
| 5,330,471 A | 7/1994 | Eggers |
| 5,330,502 A | 7/1994 | Hassler et al. |
| D349,341 S | 8/1994 | Lichtman et al. |
| 5,334,166 A | 8/1994 | Palestrant |
| 5,334,183 A | 8/1994 | Wuchinich |
| 5,334,215 A | 8/1994 | Chen |
| 5,336,220 A | 8/1994 | Ryan et al. |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,344,424 A | 9/1994 | Roberts et al. |
| 5,350,391 A | 9/1994 | Iacovelli |
| 5,352,222 A | 10/1994 | Rydell |
| 5,354,271 A | 10/1994 | Voda |
| 5,356,408 A | 10/1994 | Rydell |
| 5,359,993 A | 11/1994 | Slater et al. |
| 5,366,477 A | 11/1994 | LeMarie, III et al. |
| 5,367,250 A | 11/1994 | Whisenand |
| 5,368,600 A | 11/1994 | Failla et al. |
| 5,374,277 A | 12/1994 | Hassler |
| 5,376,089 A | 12/1994 | Smith |
| 5,376,094 A | 12/1994 | Kline |
| D354,564 S | 1/1995 | Medema |
| 5,383,875 A | 1/1995 | Bays et al. |
| 5,383,880 A | 1/1995 | Hooven |
| 5,383,897 A | 1/1995 | Wholey |
| 5,389,098 A | 2/1995 | Tsuruta et al. |
| 5,389,103 A | 2/1995 | Melzer et al. |
| 5,389,104 A | 2/1995 | Hahnen et al. |
| 5,391,166 A | 2/1995 | Eggers |
| 5,391,183 A | 2/1995 | Janzen et al. |
| 5,395,360 A | 3/1995 | Manoukian |
| 5,396,194 A | 3/1995 | Williamson et al. |
| 5,396,900 A | 3/1995 | Slater et al. |
| 5,397,325 A | 3/1995 | Della Badia et al. |
| 5,403,312 A | 4/1995 | Yates et al. |
| 5,403,342 A | 4/1995 | Tovey et al. |
| 5,405,344 A | 4/1995 | Williamson et al. |
| 5,409,763 A | 4/1995 | Serizawa et al. |
| D358,887 S | 5/1995 | Feinberg |
| 5,411,519 A | 5/1995 | Tovey et al. |
| 5,411,520 A | 5/1995 | Nash et al. |
| 5,413,571 A | 5/1995 | Katsaros et al. |
| 5,415,656 A | 5/1995 | Tihon et al. |
| 5,415,657 A | 5/1995 | Taymor-Luria |
| 5,417,709 A | 5/1995 | Slater |
| 5,422,567 A | 6/1995 | Matsunaga |
| 5,423,810 A | 6/1995 | Goble et al. |
| 5,425,690 A | 6/1995 | Chang |
| 5,425,739 A | 6/1995 | Jessen |
| 5,429,616 A | 7/1995 | Schaffer |
| 5,431,672 A | 7/1995 | Cote et al. |
| 5,431,674 A | 7/1995 | Basile et al. |
| 5,437,277 A | 8/1995 | Dumoulin et al. |
| 5,437,292 A | 8/1995 | Kipshidze et al. |
| 5,438,302 A | 8/1995 | Goble |
| 5,439,478 A | 8/1995 | Palmer |
| 5,441,517 A | 8/1995 | Kensey et al. |
| 5,443,463 A | 8/1995 | Stern et al. |
| 5,443,464 A | 8/1995 | Russell et al. |
| 5,443,479 A | 8/1995 | Bressi, Jr. |
| 5,443,480 A | 8/1995 | Jacobs et al. |
| 5,445,622 A | 8/1995 | Brown |
| 5,445,638 A | 8/1995 | Rydell et al. |
| 5,445,658 A | 8/1995 | Durrfeld et al. |
| 5,449,480 A | 9/1995 | Kuriya et al. |
| 5,451,224 A | 9/1995 | Goble et al. |
| 5,454,739 A | 10/1995 | Strand |
| 5,454,809 A | 10/1995 | Janssen |
| 5,454,823 A | 10/1995 | Richardson et al. |

(56) References Cited

U.S. PATENT DOCUMENTS

| | | |
|---|---|---|
| 5,454,827 A | 10/1995 | Aust et al. |
| 5,456,684 A | 10/1995 | Schmidt et al. |
| 5,458,598 A | 10/1995 | Feinberg et al. |
| 5,460,629 A | 10/1995 | Shlain et al. |
| 5,461,765 A | 10/1995 | Linden et al. |
| 5,462,546 A | 10/1995 | Rydell |
| 5,472,442 A | 12/1995 | Klicek |
| 5,472,443 A | 12/1995 | Cordis et al. |
| 5,476,479 A | 12/1995 | Green et al. |
| 5,478,351 A | 12/1995 | Meade et al. |
| 5,480,406 A | 1/1996 | Nolan et al. |
| 5,480,409 A | 1/1996 | Riza |
| 5,482,054 A | 1/1996 | Slater et al. |
| 5,484,436 A | 1/1996 | Eggers et al. |
| 5,493,899 A | 2/1996 | Beck et al. |
| 5,496,312 A | 3/1996 | Klicek |
| 5,496,317 A | 3/1996 | Goble et al. |
| 5,496,347 A | 3/1996 | Hashiguchi et al. |
| 5,499,997 A | 3/1996 | Sharpe et al. |
| 5,501,654 A | 3/1996 | Failla et al. |
| 5,509,922 A | 4/1996 | Aranyi et al. |
| 5,512,721 A | 4/1996 | Young et al. |
| 5,514,134 A | 5/1996 | Rydell et al. |
| 5,520,702 A | 5/1996 | Sauer et al. |
| 5,527,313 A | 6/1996 | Scott et al. |
| 5,528,833 A | 6/1996 | Sakuma |
| 5,529,067 A | 6/1996 | Larsen et al. |
| 5,531,744 A | 7/1996 | Nardella et al. |
| 5,536,251 A | 7/1996 | Evard et al. |
| 5,540,684 A | 7/1996 | Hassler, Jr. |
| 5,540,685 A | 7/1996 | Parins et al. |
| 5,540,706 A | 7/1996 | Aust et al. |
| 5,540,715 A | 7/1996 | Katsaros et al. |
| 5,542,945 A | 8/1996 | Fritzsch |
| 5,549,604 A | 8/1996 | Sutcu et al. |
| 5,554,172 A | 9/1996 | Horner et al. |
| 5,558,671 A | 9/1996 | Yates |
| 5,558,672 A | 9/1996 | Edwards et al. |
| 5,562,619 A | 10/1996 | Mirarchi et al. |
| 5,562,699 A | 10/1996 | Heimberger et al. |
| 5,562,720 A | 10/1996 | Stern et al. |
| 5,564,615 A | 10/1996 | Bishop et al. |
| 5,568,859 A | 10/1996 | Levy et al. |
| 5,569,241 A | 10/1996 | Edwards |
| 5,569,243 A | 10/1996 | Kortenbach et al. |
| 5,571,100 A | 11/1996 | Goble et al. |
| 5,573,424 A | 11/1996 | Poppe |
| 5,573,534 A | 11/1996 | Stone |
| 5,573,535 A | 11/1996 | Viklund |
| 5,575,799 A | 11/1996 | Bolanos et al. |
| 5,575,805 A | 11/1996 | Li |
| 5,578,052 A | 11/1996 | Koros et al. |
| 5,579,781 A | 12/1996 | Cooke |
| 5,582,611 A | 12/1996 | Tsuruta et al. |
| 5,582,617 A | 12/1996 | Klieman et al. |
| 5,585,896 A | 12/1996 | Yamazaki et al. |
| 5,590,570 A | 1/1997 | LeMaire, III et al. |
| 5,591,181 A | 1/1997 | Stone et al. |
| 5,597,107 A | 1/1997 | Knodel et al. |
| 5,599,350 A | 2/1997 | Schulze et al. |
| 5,601,224 A | 2/1997 | Bishop et al. |
| 5,601,601 A | 2/1997 | Tal et al. |
| 5,601,641 A | 2/1997 | Stephens |
| 5,603,711 A | 2/1997 | Parins et al. |
| 5,603,723 A | 2/1997 | Aranyi et al. |
| 5,607,436 A | 3/1997 | Pratt et al. |
| 5,611,798 A | 3/1997 | Eggers |
| 5,611,808 A | 3/1997 | Hossain et al. |
| 5,611,813 A | 3/1997 | Lichtman |
| 5,618,294 A | 4/1997 | Aust et al. |
| 5,618,307 A | 4/1997 | Donlon et al. |
| 5,620,415 A | 4/1997 | Lucey et al. |
| 5,620,453 A | 4/1997 | Nallakrishnan |
| 5,620,459 A | 4/1997 | Lichtman |
| 5,624,281 A | 4/1997 | Christensson |
| 5,624,452 A | 4/1997 | Yates |
| 5,626,578 A | 5/1997 | Tihon |
| 5,626,607 A | 5/1997 | Malecki et al. |
| 5,626,609 A | 5/1997 | Zvenyatsky et al. |
| 5,630,833 A | 5/1997 | Katsaros et al. |
| 5,637,110 A | 6/1997 | Pennybacker et al. |
| 5,637,111 A | 6/1997 | Sutcu et al. |
| 5,638,003 A | 6/1997 | Hall |
| 5,638,827 A | 6/1997 | Palmer et al. |
| 5,639,403 A | 6/1997 | Ida et al. |
| 5,643,294 A | 7/1997 | Tovey et al. |
| 5,647,869 A | 7/1997 | Goble et al. |
| 5,647,871 A | 7/1997 | Levine et al. |
| 5,649,959 A | 7/1997 | Hannam et al. |
| 5,655,650 A | 8/1997 | Naitou |
| 5,658,281 A | 8/1997 | Heard |
| D384,413 S | 9/1997 | Zlock et al. |
| 5,662,667 A | 9/1997 | Knodel |
| 5,665,100 A | 9/1997 | Yoon |
| 5,667,526 A | 9/1997 | Levin |
| 5,673,841 A | 10/1997 | Schulze et al. |
| 5,674,220 A | 10/1997 | Fox et al. |
| 5,674,229 A | 10/1997 | Tovey et al. |
| 5,681,282 A | 10/1997 | Eggers et al. |
| 5,688,270 A | 11/1997 | Yates et al. |
| 5,690,652 A | 11/1997 | Wurster et al. |
| 5,690,653 A | 11/1997 | Richardson et al. |
| 5,693,051 A | 12/1997 | Schulze et al. |
| 5,693,920 A | 12/1997 | Maeda |
| 5,695,522 A | 12/1997 | LeMaire, III et al. |
| 5,700,261 A | 12/1997 | Brinkerhoff |
| 5,700,270 A | 12/1997 | Peyser et al. |
| 5,702,390 A | 12/1997 | Austin et al. |
| 5,707,369 A | 1/1998 | Vaitekunas et al. |
| 5,709,680 A | 1/1998 | Yates et al. |
| 5,713,895 A | 2/1998 | Lontine et al. |
| 5,716,366 A | 2/1998 | Yates |
| 5,720,742 A | 2/1998 | Zacharias |
| 5,720,744 A | 2/1998 | Eggleston et al. |
| 5,722,421 A | 3/1998 | Francese et al. |
| 5,725,536 A | 3/1998 | Oberlin et al. |
| 5,727,428 A | 3/1998 | LeMaire, III et al. |
| 5,735,848 A | 4/1998 | Yates et al. |
| 5,735,849 A | 4/1998 | Baden et al. |
| 5,743,906 A | 4/1998 | Parins et al. |
| 5,752,973 A | 5/1998 | Kieturakis |
| 5,755,717 A | 5/1998 | Yates et al. |
| 5,759,188 A | 6/1998 | Yoon |
| 5,762,255 A | 6/1998 | Chrisman et al. |
| 5,762,609 A | 6/1998 | Benaron et al. |
| 5,766,130 A | 6/1998 | Selmonosky |
| 5,766,166 A | 6/1998 | Hooven |
| 5,766,170 A | 6/1998 | Eggers |
| 5,766,196 A | 6/1998 | Griffiths |
| 5,769,849 A | 6/1998 | Eggers |
| 5,772,655 A | 6/1998 | Bauer et al. |
| 5,772,670 A | 6/1998 | Brosa |
| 5,776,128 A | 7/1998 | Eggers |
| 5,776,130 A | 7/1998 | Buysse et al. |
| 5,776,156 A | 7/1998 | Shikhman |
| 5,777,519 A | 7/1998 | Simopoulos |
| 5,779,646 A | 7/1998 | Koblish et al. |
| 5,779,701 A | 7/1998 | McBrayer et al. |
| 5,779,727 A | 7/1998 | Orejola |
| 5,781,048 A | 7/1998 | Nakao et al. |
| H1745 H | 8/1998 | Paraschac |
| 5,791,231 A | 8/1998 | Cohn et al. |
| 5,792,137 A | 8/1998 | Carr et al. |
| 5,792,165 A | 8/1998 | Klieman et al. |
| 5,792,177 A | 8/1998 | Kaseda |
| 5,797,537 A | 8/1998 | Oberlin et al. |
| 5,797,927 A | 8/1998 | Yoon |
| 5,797,938 A | 8/1998 | Paraschac et al. |
| 5,797,941 A | 8/1998 | Schulze et al. |
| 5,797,958 A | 8/1998 | Yoon |
| 5,797,959 A | 8/1998 | Castro et al. |
| 5,800,448 A | 9/1998 | Banko |
| 5,800,449 A | 9/1998 | Wales |
| 5,807,393 A | 9/1998 | Williamson, IV et al. |

(56) References Cited

U.S. PATENT DOCUMENTS

| | | |
|---|---|---|
| 5,810,764 A | 9/1998 | Eggers et al. |
| 5,810,805 A | 9/1998 | Sutcu et al. |
| 5,810,808 A | 9/1998 | Eggers |
| 5,810,811 A | 9/1998 | Yates et al. |
| 5,810,877 A | 9/1998 | Roth et al. |
| 5,814,043 A | 9/1998 | Shapeton |
| 5,814,054 A | 9/1998 | Kortenbach et al. |
| 5,817,083 A | 10/1998 | Shemesh et al. |
| 5,817,119 A | 10/1998 | Klieman et al. |
| 5,820,630 A | 10/1998 | Lind |
| 5,824,978 A | 10/1998 | Karasik et al. |
| 5,827,271 A | 10/1998 | Buysse et al. |
| 5,827,274 A | 10/1998 | Bonnet et al. |
| 5,827,279 A | 10/1998 | Hughett et al. |
| 5,827,281 A | 10/1998 | Levin |
| 5,827,323 A | 10/1998 | Klieman et al. |
| 5,827,548 A | 10/1998 | Lavallee et al. |
| 5,830,212 A | 11/1998 | Cartmell et al. |
| 5,833,690 A | 11/1998 | Yates et al. |
| 5,833,695 A | 11/1998 | Yoon |
| 5,836,072 A | 11/1998 | Sullivan et al. |
| D402,028 S | 12/1998 | Grimm et al. |
| 5,843,080 A | 12/1998 | Fleenor et al. |
| 5,849,020 A | 12/1998 | Long et al. |
| 5,849,022 A | 12/1998 | Sakashita et al. |
| 5,851,214 A | 12/1998 | Larsen et al. |
| 5,853,412 A | 12/1998 | Mayenberger |
| 5,859,527 A | 1/1999 | Cook |
| 5,860,976 A | 1/1999 | Billings et al. |
| 5,865,361 A | 2/1999 | Milliman et al. |
| 5,876,401 A | 3/1999 | Schulze et al. |
| 5,876,410 A | 3/1999 | Petillo |
| 5,876,412 A | 3/1999 | Piraka |
| 5,882,567 A | 3/1999 | Cavallaro et al. |
| D408,018 S | 4/1999 | McNaughton |
| 5,891,141 A | 4/1999 | Rydell |
| 5,891,142 A | 4/1999 | Eggers et al. |
| 5,893,848 A | 4/1999 | Negus et al. |
| 5,893,863 A | 4/1999 | Yoon |
| 5,893,875 A | 4/1999 | O'Connor et al. |
| 5,893,877 A | 4/1999 | Gampp, Jr. et al. |
| 5,897,563 A | 4/1999 | Yoon et al. |
| 5,902,301 A | 5/1999 | Olig |
| 5,906,630 A | 5/1999 | Anderhub et al. |
| 5,907,140 A | 5/1999 | Smith |
| 5,908,420 A | 6/1999 | Parins et al. |
| 5,908,432 A | 6/1999 | Pan |
| 5,911,719 A | 6/1999 | Eggers |
| 5,913,874 A | 6/1999 | Berns et al. |
| 5,921,916 A | 7/1999 | Aeikens et al. |
| 5,921,984 A | 7/1999 | Sutcu et al. |
| 5,925,043 A | 7/1999 | Kumar et al. |
| 5,928,136 A | 7/1999 | Barry |
| 5,935,126 A | 8/1999 | Riza |
| 5,938,589 A | 8/1999 | Wako et al. |
| 5,941,869 A | 8/1999 | Patterson et al. |
| 5,944,562 A | 8/1999 | Christensson |
| 5,944,718 A | 8/1999 | Austin et al. |
| 5,951,545 A | 9/1999 | Schilling et al. |
| 5,951,546 A | 9/1999 | Lorentzen |
| 5,951,549 A | 9/1999 | Richardson et al. |
| 5,954,720 A | 9/1999 | Wilson et al. |
| 5,954,731 A | 9/1999 | Yoon |
| 5,954,733 A | 9/1999 | Yoon |
| 5,957,923 A | 9/1999 | Hahnen et al. |
| 5,957,937 A | 9/1999 | Yoon |
| 5,960,544 A | 10/1999 | Beyers |
| 5,961,514 A | 10/1999 | Long et al. |
| 5,964,758 A | 10/1999 | Dresden |
| 5,967,997 A | 10/1999 | Turturro et al. |
| D416,089 S | 11/1999 | Barton et al. |
| 5,976,132 A | 11/1999 | Morris |
| 5,984,932 A | 11/1999 | Yoon |
| 5,984,938 A | 11/1999 | Yoon |
| 5,984,939 A | 11/1999 | Yoon |
| 5,989,277 A | 11/1999 | LeMaire, III et al. |
| 5,993,466 A | 11/1999 | Yoon |
| 5,993,467 A | 11/1999 | Yoon |
| 5,993,474 A | 11/1999 | Ouchi |
| 5,997,565 A | 12/1999 | Inoue |
| 6,003,517 A | 12/1999 | Sheffield et al. |
| 6,004,332 A | 12/1999 | Yoon et al. |
| 6,004,335 A | 12/1999 | Vaitekunas et al. |
| 6,010,516 A | 1/2000 | Hulka |
| 6,010,519 A | 1/2000 | Mawhirt et al. |
| 6,017,354 A | 1/2000 | Culp et al. |
| 6,017,358 A | 1/2000 | Yoon et al. |
| 6,021,693 A | 2/2000 | Feng-Sing |
| 6,024,741 A | 2/2000 | Williamson, IV et al. |
| 6,024,743 A | 2/2000 | Edwards |
| 6,024,744 A | 2/2000 | Kese et al. |
| 6,027,522 A | 2/2000 | Palmer |
| 6,030,384 A | 2/2000 | Nezhat |
| 6,033,399 A | 3/2000 | Gines |
| 6,039,733 A | 3/2000 | Buysse et al. |
| 6,041,679 A | 3/2000 | Slater et al. |
| 6,050,995 A | 4/2000 | Durgin |
| 6,050,996 A | 4/2000 | Schmaltz et al. |
| 6,053,914 A | 4/2000 | Eggers et al. |
| 6,053,933 A | 4/2000 | Balazs et al. |
| D424,694 S | 5/2000 | Tetzlaff et al. |
| D425,201 S | 5/2000 | Tetzlaff et al. |
| 6,056,735 A | 5/2000 | Okada et al. |
| 6,059,782 A | 5/2000 | Novak et al. |
| 6,063,086 A | 5/2000 | Benecke et al. |
| 6,063,103 A | 5/2000 | Hashiguchi |
| 6,066,137 A | 5/2000 | Greep |
| 6,066,139 A | 5/2000 | Ryan et al. |
| 6,071,283 A | 6/2000 | Nardella et al. |
| 6,074,386 A | 6/2000 | Goble et al. |
| 6,077,287 A | 6/2000 | Taylor et al. |
| 6,080,180 A | 6/2000 | Yoon et al. |
| RE36,795 E | 7/2000 | Rydell |
| 6,083,150 A | 7/2000 | Aznoian et al. |
| 6,083,223 A | 7/2000 | Baker |
| 6,086,586 A | 7/2000 | Hooven |
| 6,086,601 A | 7/2000 | Yoon |
| 6,090,107 A | 7/2000 | Borgmeier et al. |
| 6,090,123 A | 7/2000 | Culp et al. |
| 6,096,037 A | 8/2000 | Mulier et al. |
| 6,099,537 A | 8/2000 | Sugai et al. |
| 6,099,550 A | 8/2000 | Yoon |
| 6,102,909 A | 8/2000 | Chen et al. |
| 6,106,542 A | 8/2000 | Toybin et al. |
| 6,110,171 A | 8/2000 | Rydell |
| 6,113,596 A | 9/2000 | Hooven et al. |
| 6,113,598 A | 9/2000 | Baker |
| 6,117,158 A | 9/2000 | Measamer et al. |
| 6,122,549 A | 9/2000 | Sharkey et al. |
| 6,123,701 A | 9/2000 | Nezhat |
| H1904 H | 10/2000 | Yates et al. |
| 6,126,658 A | 10/2000 | Baker |
| 6,126,665 A | 10/2000 | Yoon |
| 6,139,563 A | 10/2000 | Cosgrove, III et al. |
| 6,143,005 A | 11/2000 | Yoon et al. |
| 6,152,923 A | 11/2000 | Ryan |
| 6,152,924 A | 11/2000 | Parins |
| 6,159,217 A | 12/2000 | Robie et al. |
| 6,162,220 A | 12/2000 | Nezhat |
| 6,171,316 B1 | 1/2001 | Kovac et al. |
| 6,174,309 B1 | 1/2001 | Wrublewski et al. |
| 6,174,310 B1 | 1/2001 | Kirwan, Jr. |
| 6,178,628 B1 | 1/2001 | Clemens et al. |
| 6,179,834 B1 | 1/2001 | Buysse et al. |
| 6,179,837 B1 | 1/2001 | Hooven |
| 6,183,467 B1 | 2/2001 | Shapeton et al. |
| 6,187,003 B1 | 2/2001 | Buysse et al. |
| 6,190,386 B1 | 2/2001 | Rydell |
| 6,190,399 B1 | 2/2001 | Palmer et al. |
| 6,190,400 B1 | 2/2001 | Van De Moer et al. |
| 6,193,709 B1 | 2/2001 | Miyawaki et al. |
| 6,193,718 B1 | 2/2001 | Kortenbach et al. |
| 6,206,876 B1 | 3/2001 | Levine et al. |
| 6,206,877 B1 | 3/2001 | Kese et al. |

(56) References Cited

U.S. PATENT DOCUMENTS

| | | |
|---|---|---|
| 6,206,893 B1 | 3/2001 | Klein et al. |
| 6,214,028 B1 | 4/2001 | Yoon et al. |
| 6,217,602 B1 | 4/2001 | Redmon |
| 6,217,615 B1 | 4/2001 | Sioshansi et al. |
| 6,221,039 B1 | 4/2001 | Durgin et al. |
| 6,223,100 B1 | 4/2001 | Green |
| 6,224,593 B1 | 5/2001 | Ryan et al. |
| 6,224,614 B1 | 5/2001 | Yoon |
| 6,228,080 B1 | 5/2001 | Gines |
| 6,228,083 B1 | 5/2001 | Lands et al. |
| 6,248,124 B1 | 6/2001 | Pedros et al. |
| 6,248,944 B1 | 6/2001 | Ito |
| 6,249,706 B1 | 6/2001 | Sobota et al. |
| 6,261,307 B1 | 7/2001 | Yoon et al. |
| 6,267,758 B1 | 7/2001 | Daw et al. |
| 6,267,761 B1 | 7/2001 | Ryan |
| 6,270,497 B1 | 8/2001 | Sekino et al. |
| 6,270,508 B1 | 8/2001 | Kiernan et al. |
| 6,273,887 B1 | 8/2001 | Yamauchi et al. |
| 6,277,117 B1 | 8/2001 | Tetzlaff et al. |
| 6,280,458 B1 | 8/2001 | Bache et al. |
| 6,283,961 B1 | 9/2001 | Underwood et al. |
| D449,886 S | 10/2001 | Tetzlaff et al. |
| 6,298,550 B1 | 10/2001 | Kirwan, Jr. |
| 6,302,424 B1 | 10/2001 | Gisinger et al. |
| 6,303,166 B1 | 10/2001 | Kolbe et al. |
| 6,309,404 B1 | 10/2001 | Krzyzanowski |
| 6,319,262 B1 | 11/2001 | Bates et al. |
| 6,319,451 B1 | 11/2001 | Brune |
| 6,322,561 B1 | 11/2001 | Eggers et al. |
| 6,322,580 B1 | 11/2001 | Kanner |
| 6,325,795 B1 | 12/2001 | Lindemann et al. |
| 6,329,778 B1 | 12/2001 | Culp et al. |
| 6,334,860 B1 | 1/2002 | Dorn |
| 6,334,861 B1 | 1/2002 | Chandler et al. |
| D453,923 S | 2/2002 | Olson |
| 6,345,532 B1 | 2/2002 | Coudray et al. |
| 6,350,264 B1 | 2/2002 | Hooven |
| D454,951 S | 3/2002 | Bon |
| 6,352,536 B1 | 3/2002 | Buysse et al. |
| 6,358,249 B1 | 3/2002 | Chen et al. |
| 6,358,259 B1 | 3/2002 | Swain et al. |
| 6,358,268 B1 | 3/2002 | Hunt et al. |
| 6,361,534 B1 | 3/2002 | Chen et al. |
| 6,364,876 B1 | 4/2002 | Erb et al. |
| 6,364,879 B1 | 4/2002 | Chen et al. |
| D457,958 S | 5/2002 | Dycus et al. |
| D457,959 S | 5/2002 | Tetzlaff et al. |
| 6,385,265 B1 | 5/2002 | Duffy et al. |
| 6,387,094 B1 | 5/2002 | Eitenmuller |
| 6,391,035 B1 | 5/2002 | Appleby et al. |
| 6,398,779 B1 | 6/2002 | Buysse et al. |
| 6,402,747 B1 | 6/2002 | Lindemann et al. |
| 6,409,728 B1 | 6/2002 | Ehr et al. |
| H2037 H | 7/2002 | Yates et al. |
| 6,419,675 B1 | 7/2002 | Gallo, Sr. |
| 6,425,896 B1 | 7/2002 | Baltschun et al. |
| 6,432,112 B2 | 8/2002 | Brock et al. |
| 6,440,130 B1 | 8/2002 | Muller et al. |
| 6,440,144 B1 | 8/2002 | Bacher |
| 6,443,952 B1 | 9/2002 | Muller et al. |
| 6,443,970 B1 | 9/2002 | Schulze et al. |
| 6,451,018 B1 | 9/2002 | Lands et al. |
| 6,458,125 B1 | 10/2002 | Cosmescu |
| 6,458,128 B1 | 10/2002 | Schulze |
| 6,458,129 B2 | 10/2002 | Scarfi |
| 6,458,130 B1 | 10/2002 | Frazier et al. |
| 6,461,352 B2 | 10/2002 | Morgan et al. |
| 6,461,368 B2 | 10/2002 | Fogarty et al. |
| 6,464,701 B1 | 10/2002 | Hooven et al. |
| 6,464,702 B2 | 10/2002 | Schulze et al. |
| 6,464,704 B2 | 10/2002 | Schmaltz et al. |
| 6,471,696 B1 | 10/2002 | Berube et al. |
| D465,281 S | 11/2002 | Lang |
| D466,209 S | 11/2002 | Bon |
| 6,485,489 B2 | 11/2002 | Teirstein et al. |
| 6,488,680 B1 | 12/2002 | Francischelli et al. |
| 6,494,882 B1 | 12/2002 | Lebouitz et al. |
| 6,494,888 B1 | 12/2002 | Laufer et al. |
| 6,500,176 B1 | 12/2002 | Truckai et al. |
| 6,506,196 B1 | 1/2003 | Laufer |
| 6,508,815 B1 | 1/2003 | Strul et al. |
| 6,511,480 B1 | 1/2003 | Tetzlaff et al. |
| 6,514,215 B1 | 2/2003 | Ouchi |
| 6,514,252 B2 | 2/2003 | Nezhat et al. |
| 6,517,536 B2 | 2/2003 | Hooven et al. |
| 6,517,539 B1 | 2/2003 | Smith et al. |
| 6,527,771 B1 | 3/2003 | Weadock et al. |
| 6,533,784 B2 | 3/2003 | Truckai et al. |
| 6,537,272 B2 | 3/2003 | Christopherson et al. |
| 6,540,745 B1 | 4/2003 | Fairbourn |
| 6,545,239 B2 | 4/2003 | Spedale et al. |
| 6,554,829 B2 | 4/2003 | Schulze et al. |
| 6,554,844 B2 | 4/2003 | Lee et al. |
| 6,558,385 B1 | 5/2003 | McClurken et al. |
| 6,562,037 B2 | 5/2003 | Paton et al. |
| 6,569,105 B1 | 5/2003 | Kortenbach et al. |
| 6,582,450 B2 | 6/2003 | Ouchi |
| 6,585,735 B1 | 7/2003 | Frazier et al. |
| 6,602,252 B2 | 8/2003 | Mollenauer |
| 6,605,790 B2 | 8/2003 | Yoshida |
| 6,610,060 B2 | 8/2003 | Mulier et al. |
| 6,613,048 B2 | 9/2003 | Mulier et al. |
| 6,616,654 B2 | 9/2003 | Mollenauer |
| 6,616,658 B2 | 9/2003 | Ineson |
| 6,616,661 B2 | 9/2003 | Wellman et al. |
| 6,620,161 B2 | 9/2003 | Schulze et al. |
| 6,620,184 B2 | 9/2003 | de Laforcade et al. |
| 6,623,482 B2 | 9/2003 | Pendekanti et al. |
| 6,626,901 B1 | 9/2003 | Treat et al. |
| 6,629,534 B1 | 10/2003 | St. Goar et al. |
| 6,638,287 B2 | 10/2003 | Danitz et al. |
| 6,641,595 B1 | 11/2003 | Moran et al. |
| 6,652,514 B2 | 11/2003 | Ellman et al. |
| 6,652,518 B2 | 11/2003 | Wellman et al. |
| 6,652,521 B2 | 11/2003 | Schulze |
| 6,656,173 B1 | 12/2003 | Palermo |
| 6,656,175 B2 | 12/2003 | Francischelli et al. |
| 6,656,177 B2 | 12/2003 | Truckai et al. |
| 6,660,072 B2 | 12/2003 | Chatterjee |
| 6,663,639 B1 | 12/2003 | Laufer et al. |
| 6,663,641 B1 | 12/2003 | Kovac et al. |
| 6,666,854 B1 | 12/2003 | Lange |
| 6,666,862 B2 | 12/2003 | Jain et al. |
| 6,669,696 B2 | 12/2003 | Bacher et al. |
| 6,673,092 B1 | 1/2004 | Bacher |
| 6,676,660 B2 | 1/2004 | Wampler et al. |
| 6,676,676 B2 | 1/2004 | Danitz et al. |
| 6,679,882 B1 | 1/2004 | Kornerup |
| 6,682,527 B2 | 1/2004 | Strul |
| 6,682,528 B2 | 1/2004 | Frazier et al. |
| 6,685,704 B2 | 2/2004 | Greep |
| 6,685,724 B1 | 2/2004 | Haluck |
| 6,689,131 B2 | 2/2004 | McClurken |
| 6,692,445 B2 | 2/2004 | Roberts et al. |
| 6,693,246 B1 | 2/2004 | Rudolph et al. |
| 6,695,840 B2 | 2/2004 | Schulze |
| 6,702,810 B2 | 3/2004 | McClurken et al. |
| 6,709,445 B2 | 3/2004 | Boebel et al. |
| 6,723,092 B2 | 4/2004 | Brown et al. |
| 6,726,068 B2 | 4/2004 | Miller |
| 6,726,686 B2 | 4/2004 | Buysse et al. |
| 6,726,694 B2 | 4/2004 | Blatter et al. |
| 6,733,498 B2 | 5/2004 | Paton et al. |
| 6,733,501 B2 | 5/2004 | Levine |
| 6,736,813 B2 | 5/2004 | Yamauchi et al. |
| 6,743,229 B2 | 6/2004 | Buysse et al. |
| 6,743,230 B2 | 6/2004 | Lutze et al. |
| 6,743,239 B1 | 6/2004 | Kuehn et al. |
| 6,743,240 B2 | 6/2004 | Smith et al. |
| 6,755,338 B2 | 6/2004 | Hahnen et al. |
| 6,755,824 B2 | 6/2004 | Jain et al. |
| 6,755,843 B2 | 6/2004 | Chung et al. |
| 6,756,553 B1 | 6/2004 | Yamaguchi et al. |

(56) References Cited

U.S. PATENT DOCUMENTS

| | | |
|---|---|---|
| 6,757,977 B2 | 7/2004 | Dambal et al. |
| 6,758,846 B2 | 7/2004 | Goble et al. |
| D493,888 S | 8/2004 | Reschke |
| 6,770,072 B1 | 8/2004 | Truckai et al. |
| 6,773,409 B2 | 8/2004 | Truckai et al. |
| 6,773,432 B1 | 8/2004 | Clayman et al. |
| 6,773,434 B2 | 8/2004 | Ciarrocca |
| 6,773,435 B2 | 8/2004 | Schulze et al. |
| 6,773,441 B1 | 8/2004 | Laufer et al. |
| 6,775,575 B2 | 8/2004 | Bommannan et al. |
| 6,776,780 B2 | 8/2004 | Mulier et al. |
| 6,780,181 B2 | 8/2004 | Kroll et al. |
| 6,784,405 B2 | 8/2004 | Flugstad et al. |
| 6,786,905 B2 | 9/2004 | Swanson et al. |
| 6,790,217 B2 | 9/2004 | Schulze et al. |
| 6,796,981 B2 | 9/2004 | Wham et al. |
| D496,997 S | 10/2004 | Dycus et al. |
| 6,800,825 B1 | 10/2004 | Sasaki et al. |
| 6,802,843 B2 | 10/2004 | Truckai et al. |
| 6,808,525 B2 | 10/2004 | Latterell et al. |
| D499,181 S | 11/2004 | Dycus et al. |
| 6,818,000 B2 | 11/2004 | Muller et al. |
| 6,818,007 B1 | 11/2004 | Dampney et al. |
| 6,821,273 B2 | 11/2004 | Mollenauer |
| 6,821,285 B2 | 11/2004 | Laufer et al. |
| 6,824,547 B2 | 11/2004 | Wilson, Jr. et al. |
| 6,830,174 B2 | 12/2004 | Hillstead et al. |
| 6,835,200 B2 | 12/2004 | Laufer et al. |
| 6,843,789 B2 | 1/2005 | Goble |
| 6,857,357 B2 | 2/2005 | Fujii |
| 6,858,028 B2 | 2/2005 | Mulier et al. |
| D502,994 S | 3/2005 | Blake, III |
| 6,860,880 B2 | 3/2005 | Treat et al. |
| 6,878,147 B2 | 4/2005 | Prakash et al. |
| 6,887,240 B1 | 5/2005 | Lands et al. |
| 6,889,116 B2 | 5/2005 | Jinno |
| 6,905,497 B2 | 6/2005 | Truckai et al. |
| 6,908,463 B2 | 6/2005 | Treat et al. |
| 6,914,201 B2 | 7/2005 | Van Vooren et al. |
| 6,926,716 B2 | 8/2005 | Baker et al. |
| 6,929,644 B2 | 8/2005 | Truckai et al. |
| 6,932,810 B2 | 8/2005 | Ryan |
| 6,932,816 B2 | 8/2005 | Phan |
| 6,934,134 B2 | 8/2005 | Mori et al. |
| 6,936,061 B2 | 8/2005 | Sasaki |
| D509,297 S | 9/2005 | Wells |
| 6,942,662 B2 | 9/2005 | Goble et al. |
| 6,943,311 B2 | 9/2005 | Miyako |
| 6,951,559 B1 | 10/2005 | Greep |
| 6,953,430 B2 | 10/2005 | Kidooka |
| 6,953,461 B2 | 10/2005 | McClurken et al. |
| 6,958,070 B2 | 10/2005 | Witt et al. |
| 6,960,210 B2 | 11/2005 | Lands et al. |
| 6,964,662 B2 | 11/2005 | Kidooka |
| 6,966,907 B2 | 11/2005 | Goble |
| 6,972,017 B2 | 12/2005 | Smith et al. |
| 6,974,452 B1 | 12/2005 | Gille et al. |
| 6,976,492 B2 | 12/2005 | Ingle et al. |
| 6,976,992 B2 | 12/2005 | Sachatello et al. |
| 6,977,495 B2 | 12/2005 | Donofrio |
| 6,979,786 B2 | 12/2005 | Aukland et al. |
| 6,981,628 B2 | 1/2006 | Wales |
| 6,987,244 B2 | 1/2006 | Bauer |
| 6,989,010 B2 | 1/2006 | Francischelli et al. |
| 6,989,017 B2 | 1/2006 | Howell et al. |
| 6,994,707 B2 | 2/2006 | Ellman et al. |
| 6,994,709 B2 | 2/2006 | Iida |
| 6,997,931 B2 | 2/2006 | Sauer et al. |
| 7,001,381 B2 | 2/2006 | Harano et al. |
| 7,001,408 B2 | 2/2006 | Knodel et al. |
| 7,011,657 B2 | 3/2006 | Truckai et al. |
| 7,025,763 B2 | 4/2006 | Karasawa et al. |
| 7,033,354 B2 | 4/2006 | Keppel |
| 7,033,356 B2 | 4/2006 | Latterell et al. |
| 7,041,102 B2 | 5/2006 | Truckai et al. |
| 7,044,948 B2 | 5/2006 | Keppel |
| 7,052,489 B2 | 5/2006 | Griego et al. |
| 7,052,496 B2 | 5/2006 | Yamauchi |
| 7,063,699 B2 | 6/2006 | Hess et al. |
| 7,063,715 B2 | 6/2006 | Onuki et al. |
| D525,361 S | 7/2006 | Hushka |
| 7,070,597 B2 | 7/2006 | Truckai et al. |
| 7,083,480 B2 | 8/2006 | Silber |
| 7,083,618 B2 | 8/2006 | Couture et al. |
| 7,083,619 B2 | 8/2006 | Truckai et al. |
| 7,083,620 B2 | 8/2006 | Jahns et al. |
| 7,087,051 B2 | 8/2006 | Bourne et al. |
| 7,087,054 B2 | 8/2006 | Truckai et al. |
| 7,090,673 B2 | 8/2006 | Dycus et al. |
| 7,090,689 B2 | 8/2006 | Nagase et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,103,947 B2 | 9/2006 | Sartor et al. |
| 7,107,124 B2 | 9/2006 | Green |
| 7,108,694 B2 | 9/2006 | Miura et al. |
| 7,112,199 B2 | 9/2006 | Cosmescu |
| 7,112,201 B2 | 9/2006 | Truckai et al. |
| D531,311 S | 10/2006 | Guerra et al. |
| 7,115,123 B2 | 10/2006 | Knowlton et al. |
| 7,115,139 B2 | 10/2006 | McClurken et al. |
| 7,118,570 B2 | 10/2006 | Tetzlaff et al. |
| 7,118,587 B2 | 10/2006 | Dycus et al. |
| 7,131,860 B2 | 11/2006 | Sartor et al. |
| 7,131,970 B2 | 11/2006 | Moses et al. |
| 7,131,971 B2 | 11/2006 | Dycus et al. |
| 7,135,018 B2 | 11/2006 | Ryan et al. |
| 7,135,020 B2 | 11/2006 | Lawes et al. |
| 7,137,980 B2 | 11/2006 | Buysse et al. |
| D533,274 S | 12/2006 | Visconti et al. |
| D533,942 S | 12/2006 | Kerr et al. |
| 7,145,757 B2 | 12/2006 | Shea et al. |
| 7,147,632 B2 | 12/2006 | Prakash et al. |
| 7,147,638 B2 | 12/2006 | Chapman et al. |
| 7,150,097 B2 | 12/2006 | Sremcich et al. |
| 7,150,749 B2 | 12/2006 | Dycus et al. |
| 7,153,314 B2 | 12/2006 | Laufer et al. |
| D535,027 S | 1/2007 | James et al. |
| 7,156,842 B2 | 1/2007 | Sartor et al. |
| 7,156,846 B2 | 1/2007 | Dycus et al. |
| 7,160,298 B2 | 1/2007 | Lawes et al. |
| 7,160,299 B2 | 1/2007 | Baily |
| 7,166,106 B2 | 1/2007 | Bartel et al. |
| 7,169,145 B2 | 1/2007 | Isaacson et al. |
| 7,169,146 B2 | 1/2007 | Truckai et al. |
| 7,179,255 B2 | 2/2007 | Lettice et al. |
| 7,179,258 B2 | 2/2007 | Buysse et al. |
| 7,184,820 B2 | 2/2007 | Jersey-Willuhn et al. |
| D538,932 S | 3/2007 | Malik |
| 7,189,233 B2 | 3/2007 | Truckai et al. |
| 7,195,631 B2 | 3/2007 | Dumbauld |
| D541,418 S | 4/2007 | Schechter et al. |
| 7,204,832 B2 | 4/2007 | Altshuler et al. |
| 7,204,835 B2 | 4/2007 | Latterell et al. |
| 7,207,990 B2 | 4/2007 | Lands et al. |
| 7,208,005 B2 | 4/2007 | Frecker et al. |
| D541,611 S | 5/2007 | Aglassinger |
| D541,938 S | 5/2007 | Kerr et al. |
| 7,211,084 B2 | 5/2007 | Goble et al. |
| 7,223,264 B2 | 5/2007 | Daniel et al. |
| 7,223,265 B2 | 5/2007 | Keppel |
| D545,432 S | 6/2007 | Watanabe |
| 7,232,440 B2 | 6/2007 | Dumbauld et al. |
| D547,154 S | 7/2007 | Lee |
| 7,238,184 B2 | 7/2007 | Megerman et al. |
| 7,241,288 B2 | 7/2007 | Braun |
| 7,241,296 B2 | 7/2007 | Buysse et al. |
| 7,244,257 B2 | 7/2007 | Podhajsky et al. |
| 7,246,734 B2 | 7/2007 | Shelton, IV |
| 7,248,944 B2 | 7/2007 | Green |
| 7,252,667 B2 | 8/2007 | Moses et al. |
| 7,254,433 B2 | 8/2007 | Diab et al. |
| 7,255,697 B2 | 8/2007 | Dycus et al. |
| 7,258,688 B1 | 8/2007 | Shah et al. |

(56) References Cited

U.S. PATENT DOCUMENTS

| | | |
|---|---|---|
| 7,267,677 B2 | 9/2007 | Johnson et al. |
| 7,270,660 B2 | 9/2007 | Ryan |
| 7,270,664 B2 | 9/2007 | Johnson et al. |
| 7,276,068 B2 | 10/2007 | Johnson et al. |
| 7,288,103 B2 | 10/2007 | Suzuki |
| 7,291,161 B2 | 11/2007 | Hooven |
| 7,300,435 B2 | 11/2007 | Wham et al. |
| 7,303,557 B2 | 12/2007 | Wham et al. |
| 7,311,709 B2 | 12/2007 | Truckai et al. |
| 7,314,471 B2 | 1/2008 | Holman |
| 7,318,823 B2 | 1/2008 | Sharps et al. |
| 7,326,202 B2 | 2/2008 | McGaffigan |
| 7,329,256 B2 | 2/2008 | Johnson et al. |
| 7,329,257 B2 | 2/2008 | Kanehira et al. |
| D564,662 S | 3/2008 | Moses et al. |
| 7,338,526 B2 | 3/2008 | Steinberg |
| 7,342,754 B2 | 3/2008 | Fitzgerald et al. |
| 7,344,268 B2 | 3/2008 | Jigamian |
| 7,347,864 B2 | 3/2008 | Vargas |
| D567,943 S | 4/2008 | Moses et al. |
| 7,354,440 B2 | 4/2008 | Truckal et al. |
| 7,361,172 B2 | 4/2008 | Cimino |
| 7,367,976 B2 | 5/2008 | Lawes et al. |
| 7,377,920 B2 | 5/2008 | Buysse et al. |
| 7,384,420 B2 | 6/2008 | Dycus et al. |
| 7,384,421 B2 | 6/2008 | Hushka |
| 7,396,265 B2 | 7/2008 | Darley et al. |
| 7,396,336 B2 | 7/2008 | Orszulak et al. |
| 7,396,356 B2 | 7/2008 | Mollenauer |
| D575,395 S | 8/2008 | Hushka |
| D575,401 S | 8/2008 | Hixson et al. |
| 7,422,592 B2 | 9/2008 | Morley et al. |
| 7,425,835 B2 | 9/2008 | Eisele |
| 7,431,721 B2 | 10/2008 | Paton et al. |
| 7,435,249 B2 | 10/2008 | Buysse et al. |
| 7,438,714 B2 | 10/2008 | Phan |
| 7,442,193 B2 | 10/2008 | Shields et al. |
| 7,442,194 B2 | 10/2008 | Dumbauld et al. |
| 7,445,621 B2 | 11/2008 | Dumbauld et al. |
| D582,038 S | 12/2008 | Swoyer et al. |
| 7,458,972 B2 | 12/2008 | Keppel |
| 7,473,253 B2 | 1/2009 | Dycus et al. |
| 7,481,810 B2 | 1/2009 | Dumbauld et al. |
| 7,487,780 B2 | 2/2009 | Hooven |
| 7,491,201 B2 | 2/2009 | Shields et al. |
| 7,491,202 B2 | 2/2009 | Odom et al. |
| 7,500,975 B2 | 3/2009 | Cunningham et al. |
| 7,503,474 B2 | 3/2009 | Hillstead et al. |
| 7,510,556 B2 | 3/2009 | Nguyen et al. |
| 7,513,898 B2 | 4/2009 | Johnson et al. |
| 7,517,351 B2 | 4/2009 | Culp et al. |
| 7,540,872 B2 | 6/2009 | Schechter et al. |
| 7,549,995 B2 | 6/2009 | Schultz |
| 7,553,312 B2 | 6/2009 | Tetzlaff et al. |
| 7,553,686 B2 | 6/2009 | George et al. |
| 7,569,626 B2 | 8/2009 | Truckai |
| 7,582,087 B2 | 9/2009 | Tetzlaff et al. |
| 7,588,565 B2 | 9/2009 | Marchitto et al. |
| 7,594,313 B2 | 9/2009 | Prakash et al. |
| 7,594,916 B2 | 9/2009 | Weinberg |
| 7,597,693 B2 | 10/2009 | Garrison |
| 7,621,910 B2 | 11/2009 | Sugi |
| 7,624,186 B2 | 11/2009 | Tanida |
| 7,625,370 B2 | 12/2009 | Hart et al. |
| 7,628,791 B2 | 12/2009 | Garrison et al. |
| 7,628,792 B2 | 12/2009 | Guerra |
| 7,637,409 B2 | 12/2009 | Marczyk |
| 7,641,653 B2 | 1/2010 | Dalla Betta et al. |
| 7,651,493 B2 | 1/2010 | Arts et al. |
| 7,651,494 B2 | 1/2010 | McClurken et al. |
| 7,655,004 B2 | 2/2010 | Long |
| 7,655,007 B2 | 2/2010 | Baily |
| 7,668,597 B2 | 2/2010 | Engmark et al. |
| 7,678,111 B2 | 3/2010 | Mulier et al. |
| 7,686,804 B2 | 3/2010 | Johnson et al. |
| 7,686,827 B2 | 3/2010 | Hushka |
| 7,708,735 B2 | 5/2010 | Chapman et al. |
| 7,717,115 B2 | 5/2010 | Barrett et al. |
| 7,717,904 B2 | 5/2010 | Suzuki et al. |
| 7,717,914 B2 | 5/2010 | Kimura |
| 7,717,915 B2 | 5/2010 | Miyazawa |
| 7,722,607 B2 | 5/2010 | Dumbauld et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| 7,727,231 B2 | 6/2010 | Swanson |
| 7,731,717 B2 | 6/2010 | Odom et al. |
| 7,736,374 B2 | 6/2010 | Vaughan et al. |
| 7,744,615 B2 | 6/2010 | Couture |
| 7,749,217 B2 | 7/2010 | Podhajsky |
| 7,753,908 B2 | 7/2010 | Swanson |
| 7,753,909 B2 | 7/2010 | Chapman et al. |
| D621,503 S | 8/2010 | Otten et al. |
| 7,766,910 B2 | 8/2010 | Hixson et al. |
| 7,771,425 B2 | 8/2010 | Dycus et al. |
| 7,776,036 B2 | 8/2010 | Schechter et al. |
| 7,776,037 B2 | 8/2010 | Odom |
| 7,780,662 B2 | 8/2010 | Bahney |
| 7,780,663 B2 | 8/2010 | Yates et al. |
| 7,789,878 B2 | 9/2010 | Dumbauld et al. |
| 7,799,026 B2 | 9/2010 | Schechter et al. |
| 7,799,028 B2 | 9/2010 | Schechter et al. |
| 7,806,892 B2 | 10/2010 | Makin et al. |
| 7,811,283 B2 | 10/2010 | Moses et al. |
| 7,819,872 B2 | 10/2010 | Johnson et al. |
| D627,462 S | 11/2010 | Kingsley |
| D628,289 S | 11/2010 | Romero |
| D628,290 S | 11/2010 | Romero |
| 7,828,798 B2 | 11/2010 | Buysse et al. |
| 7,832,408 B2 | 11/2010 | Shelton, IV et al. |
| 7,837,685 B2 | 11/2010 | Weinberg et al. |
| 7,839,674 B2 | 11/2010 | Lowrey et al. |
| 7,842,033 B2 | 11/2010 | Isaacson et al. |
| 7,846,158 B2 | 12/2010 | Podhajsky |
| 7,846,161 B2 | 12/2010 | Dumbauld et al. |
| 7,857,812 B2 | 12/2010 | Dycus et al. |
| D630,324 S | 1/2011 | Reschke |
| 7,877,852 B2 | 2/2011 | Unger et al. |
| 7,877,853 B2 | 2/2011 | Unger et al. |
| 7,879,035 B2 | 2/2011 | Garrison et al. |
| 7,887,535 B2 | 2/2011 | Lands et al. |
| 7,887,536 B2 | 2/2011 | Johnson et al. |
| 7,896,878 B2 | 3/2011 | Johnson et al. |
| 7,898,288 B2 | 3/2011 | Wong |
| 7,900,805 B2 | 3/2011 | Shelton, IV et al. |
| 7,901,400 B2 | 3/2011 | Wham et al. |
| 7,905,380 B2 | 3/2011 | Shelton, IV et al. |
| 7,905,881 B2 | 3/2011 | Masuda et al. |
| 7,909,820 B2 | 3/2011 | Lipson et al. |
| 7,909,823 B2 | 3/2011 | Moses et al. |
| 7,909,824 B2 | 3/2011 | Masuda et al. |
| 7,918,848 B2 | 4/2011 | Lau et al. |
| 7,922,718 B2 | 4/2011 | Moses et al. |
| 7,922,742 B2 | 4/2011 | Hillstead et al. |
| 7,922,953 B2 | 4/2011 | Guerra |
| 7,931,649 B2 | 4/2011 | Couture et al. |
| 7,935,052 B2 | 5/2011 | Dumbauld |
| 7,945,332 B2 | 5/2011 | Schechter |
| 7,947,041 B2 | 5/2011 | Tetzlaff et al. |
| 7,949,407 B2 | 5/2011 | Kaplan et al. |
| 7,951,149 B2 | 5/2011 | Carlton |
| 7,951,150 B2 | 5/2011 | Johnson et al. |
| 7,955,326 B2 | 6/2011 | Paul et al. |
| 7,955,327 B2 | 6/2011 | Sartor et al. |
| 7,955,331 B2 | 6/2011 | Truckai et al. |
| 7,955,332 B2 | 6/2011 | Arts et al. |
| 7,963,965 B2 | 6/2011 | Buysse et al. |
| 7,967,839 B2 | 6/2011 | Flock et al. |
| 7,972,328 B2 | 7/2011 | Wham et al. |
| 7,972,331 B2 | 7/2011 | Hafner |
| 7,976,544 B2 | 7/2011 | McClurken et al. |
| 7,981,113 B2 | 7/2011 | Truckai et al. |

(56) References Cited

U.S. PATENT DOCUMENTS

| | | |
|---|---|---|
| 7,988,507 B2 | 8/2011 | Darley et al. |
| 7,998,095 B2 | 8/2011 | McAuley |
| 8,012,150 B2 | 9/2011 | Wham et al. |
| 8,016,827 B2 | 9/2011 | Chojin |
| 8,034,049 B2 | 10/2011 | Odom et al. |
| D649,249 S | 11/2011 | Guerra |
| D649,643 S | 11/2011 | Allen, IV et al. |
| 8,048,074 B2 | 11/2011 | Masuda |
| 8,070,746 B2 | 12/2011 | Orton et al. |
| 8,070,748 B2 | 12/2011 | Hixson et al. |
| 8,075,580 B2 | 12/2011 | Makower |
| 8,089,417 B2 | 1/2012 | Popovic et al. |
| 8,092,451 B2 | 1/2012 | Schechter et al. |
| 8,104,956 B2 | 1/2012 | Blaha |
| 8,112,871 B2 | 2/2012 | Brandt et al. |
| 8,114,122 B2 | 2/2012 | Nau, Jr. |
| 8,123,743 B2 | 2/2012 | Arts et al. |
| 8,128,624 B2 | 3/2012 | Couture et al. |
| 8,128,625 B2 | 3/2012 | Odom |
| 8,133,224 B2 | 3/2012 | Geiselhart |
| 8,133,254 B2 | 3/2012 | Dumbauld et al. |
| 8,142,425 B2 | 3/2012 | Eggers |
| 8,142,473 B2 | 3/2012 | Cunningham |
| 8,147,485 B2 | 4/2012 | Wham et al. |
| 8,147,489 B2 | 4/2012 | Moses et al. |
| 8,157,145 B2 | 4/2012 | Shelton, IV et al. |
| 8,161,977 B2 | 4/2012 | Shelton, IV et al. |
| 8,162,940 B2 | 4/2012 | Johnson et al. |
| 8,162,965 B2 | 4/2012 | Reschke et al. |
| 8,162,973 B2 | 4/2012 | Cunningham |
| 8,177,794 B2 | 5/2012 | Cabrera et al. |
| 8,181,649 B2 | 5/2012 | Brunner |
| 8,182,476 B2 | 5/2012 | Julian et al. |
| 8,187,273 B2 | 5/2012 | Kerr et al. |
| D661,394 S | 6/2012 | Romero et al. |
| 8,192,433 B2 | 6/2012 | Johnson et al. |
| 8,192,444 B2 | 6/2012 | Dycus |
| 8,197,479 B2 | 6/2012 | Olson et al. |
| 8,197,633 B2 | 6/2012 | Guerra |
| 8,207,651 B2 | 6/2012 | Gilbert |
| 8,211,105 B2 | 7/2012 | Buysse et al. |
| 8,215,182 B2 | 7/2012 | Artale et al. |
| 8,216,223 B2 | 7/2012 | Wham et al. |
| 8,221,416 B2 | 7/2012 | Townsend |
| 8,226,650 B2 | 7/2012 | Kerr |
| 8,235,992 B2 | 8/2012 | Guerra et al. |
| 8,235,993 B2 | 8/2012 | Hushka et al. |
| 8,236,025 B2 | 8/2012 | Hushka et al. |
| 8,241,282 B2 | 8/2012 | Unger et al. |
| 8,241,283 B2 | 8/2012 | Guerra et al. |
| 8,241,284 B2 | 8/2012 | Dycus et al. |
| 8,246,618 B2 | 8/2012 | Bucciaglia et al. |
| 8,251,994 B2 | 8/2012 | McKenna et al. |
| 8,251,996 B2 | 8/2012 | Hushka et al. |
| 8,257,352 B2 | 9/2012 | Lawes et al. |
| 8,257,387 B2 | 9/2012 | Cunningham |
| 9,113,940 B2 | 8/2015 | Twomey |
| 2002/0029036 A1 | 3/2002 | Goble et al. |
| 2002/0107517 A1 | 8/2002 | Witt et al. |
| 2002/0111624 A1 | 8/2002 | Witt et al. |
| 2002/0165469 A1 | 11/2002 | Murakami |
| 2003/0014052 A1 | 1/2003 | Buysse et al. |
| 2003/0014053 A1 | 1/2003 | Nguyen et al. |
| 2003/0018332 A1 | 1/2003 | Schmaltz et al. |
| 2003/0069570 A1 | 4/2003 | Witzel et al. |
| 2003/0109875 A1 | 6/2003 | Tetzlaff et al. |
| 2003/0114851 A1 | 6/2003 | Truckai et al. |
| 2003/0130653 A1 | 7/2003 | Sixto et al. |
| 2003/0139741 A1 | 7/2003 | Goble et al. |
| 2003/0158548 A1 | 8/2003 | Phan et al. |
| 2003/0171747 A1 | 9/2003 | Kanehira et al. |
| 2003/0181898 A1 | 9/2003 | Bowers |
| 2003/0181910 A1 | 9/2003 | Dycus et al. |
| 2003/0191396 A1 | 10/2003 | Sanghvi et al. |
| 2003/0216732 A1 | 11/2003 | Truckai et al. |
| 2003/0229344 A1 | 12/2003 | Dycus et al. |
| 2003/0236325 A1 | 12/2003 | Bonora |
| 2004/0030330 A1 | 2/2004 | Brassell et al. |
| 2004/0064151 A1 | 4/2004 | Mollenauer |
| 2004/0115296 A1 | 6/2004 | Duffin |
| 2004/0176779 A1 | 9/2004 | Casutt et al. |
| 2004/0199181 A1 | 10/2004 | Knodel et al. |
| 2004/0224590 A1 | 11/2004 | Rawa et al. |
| 2004/0236326 A1 | 11/2004 | Schulze et al. |
| 2004/0249374 A1 | 12/2004 | Tetzlaff et al. |
| 2004/0260281 A1 | 12/2004 | Baxter et al. |
| 2005/0004569 A1 | 1/2005 | Witt et al. |
| 2005/0033278 A1 | 2/2005 | McClurken et al. |
| 2005/0059858 A1 | 3/2005 | Frith et al. |
| 2005/0059934 A1 | 3/2005 | Wenchell et al. |
| 2005/0090817 A1 | 4/2005 | Phan |
| 2005/0096645 A1 | 5/2005 | Wellman et al. |
| 2005/0149017 A1 | 7/2005 | Dycus |
| 2005/0222560 A1 | 10/2005 | Kimura et al. |
| 2005/0254081 A1 | 11/2005 | Ryu et al. |
| 2005/0261588 A1 | 11/2005 | Makin et al. |
| 2005/0283148 A1 | 12/2005 | Janssen et al. |
| 2006/0052779 A1 | 3/2006 | Hammill |
| 2006/0064086 A1 | 3/2006 | Odom |
| 2006/0079933 A1 | 4/2006 | Hushka et al. |
| 2006/0084973 A1 | 4/2006 | Hushka |
| 2006/0111711 A1 | 5/2006 | Goble |
| 2006/0173452 A1 | 8/2006 | Buysse et al. |
| 2006/0189981 A1* | 8/2006 | Dycus ............... A61B 18/1445 606/51 |
| 2006/0190035 A1 | 8/2006 | Hushka et al. |
| 2006/0224053 A1 | 10/2006 | Black et al. |
| 2006/0253126 A1 | 11/2006 | Bjerken et al. |
| 2006/0259036 A1 | 11/2006 | Tetzlaff et al. |
| 2006/0264922 A1 | 11/2006 | Sartor et al. |
| 2006/0271030 A1 | 11/2006 | Francis et al. |
| 2006/0283093 A1 | 12/2006 | Petrovic et al. |
| 2006/0287641 A1 | 12/2006 | Perlin |
| 2007/0027447 A1 | 2/2007 | Theroux et al. |
| 2007/0043353 A1 | 2/2007 | Dycus et al. |
| 2007/0062017 A1 | 3/2007 | Dycus et al. |
| 2007/0118115 A1 | 5/2007 | Artale et al. |
| 2007/0173811 A1 | 7/2007 | Couture et al. |
| 2007/0173813 A1 | 7/2007 | Odom |
| 2007/0198011 A1 | 8/2007 | Sugita |
| 2007/0225695 A1 | 9/2007 | Mayer et al. |
| 2007/0260238 A1 | 11/2007 | Guerra |
| 2007/0260242 A1 | 11/2007 | Dycus et al. |
| 2007/0265616 A1 | 11/2007 | Couture et al. |
| 2007/0265620 A1 | 11/2007 | Kraas et al. |
| 2008/0004616 A1 | 1/2008 | Patrick |
| 2008/0015563 A1 | 1/2008 | Hoey et al. |
| 2008/0015575 A1 | 1/2008 | Odom et al. |
| 2008/0033428 A1 | 2/2008 | Artale et al. |
| 2008/0046122 A1 | 2/2008 | Manzo et al. |
| 2008/0058802 A1 | 3/2008 | Couture et al. |
| 2008/0125797 A1 | 5/2008 | Kelleher |
| 2008/0171938 A1 | 7/2008 | Masuda et al. |
| 2008/0172051 A1 | 7/2008 | Masuda et al. |
| 2008/0215050 A1 | 9/2008 | Bakos |
| 2008/0234672 A1 | 9/2008 | Bastian |
| 2008/0234701 A1 | 9/2008 | Morales et al. |
| 2008/0243106 A1 | 10/2008 | Coe et al. |
| 2008/0243120 A1 | 10/2008 | Lawes et al. |
| 2008/0243158 A1 | 10/2008 | Morgan |
| 2008/0249523 A1 | 10/2008 | McPherson et al. |
| 2008/0249527 A1 | 10/2008 | Couture |
| 2008/0271360 A1 | 11/2008 | Barfield |
| 2008/0281311 A1 | 11/2008 | Dunning et al. |
| 2008/0319292 A1 | 12/2008 | Say et al. |
| 2008/0319442 A1 | 12/2008 | Unger et al. |
| 2009/0012520 A1 | 1/2009 | Hixson et al. |
| 2009/0012556 A1 | 1/2009 | Boudreaux et al. |
| 2009/0024126 A1 | 1/2009 | Artale et al. |
| 2009/0036881 A1 | 2/2009 | Artale et al. |
| 2009/0036899 A1 | 2/2009 | Carlton et al. |
| 2009/0043304 A1 | 2/2009 | Tetzlaff et al. |
| 2009/0048596 A1 | 2/2009 | Shields et al. |
| 2009/0054894 A1 | 2/2009 | Yachi |

(56) References Cited

U.S. PATENT DOCUMENTS

| | | |
|---|---|---|
| 2009/0062794 A1 | 3/2009 | Buysse et al. |
| 2009/0065565 A1 | 3/2009 | Cao |
| 2009/0076506 A1 | 3/2009 | Baker |
| 2009/0082766 A1 | 3/2009 | Unger et al. |
| 2009/0088739 A1 | 4/2009 | Hushka et al. |
| 2009/0088745 A1 | 4/2009 | Hushka et al. |
| 2009/0088746 A1 | 4/2009 | Hushka et al. |
| 2009/0088748 A1 | 4/2009 | Guerra et al. |
| 2009/0088750 A1 | 4/2009 | Hushka et al. |
| 2009/0105750 A1 | 4/2009 | Price et al. |
| 2009/0112206 A1 | 4/2009 | Dumbauld et al. |
| 2009/0112229 A1 | 4/2009 | Omori et al. |
| 2009/0131934 A1 | 5/2009 | Odom et al. |
| 2009/0138003 A1 | 5/2009 | Deville et al. |
| 2009/0138006 A1 | 5/2009 | Bales et al. |
| 2009/0149853 A1 | 6/2009 | Shields et al. |
| 2009/0149854 A1 | 6/2009 | Cunningham et al. |
| 2009/0157071 A1 | 6/2009 | Wham et al. |
| 2009/0171354 A1 | 7/2009 | Deville et al. |
| 2009/0177094 A1 | 7/2009 | Brown et al. |
| 2009/0182327 A1 | 7/2009 | Unger |
| 2009/0187188 A1 | 7/2009 | Guerra et al. |
| 2009/0198233 A1 | 8/2009 | Chojin |
| 2009/0204114 A1 | 8/2009 | Odom |
| 2009/0204137 A1 | 8/2009 | Maxwell |
| 2009/0206126 A1 | 8/2009 | Huitema et al. |
| 2009/0209957 A1 | 8/2009 | Schmaltz et al. |
| 2009/0209960 A1 | 8/2009 | Chojin |
| 2009/0234354 A1 | 9/2009 | Johnson et al. |
| 2009/0248007 A1 | 10/2009 | Falkenstein et al. |
| 2009/0248013 A1 | 10/2009 | Falkenstein et al. |
| 2009/0248019 A1 | 10/2009 | Falkenstein et al. |
| 2009/0248020 A1 | 10/2009 | Falkenstein et al. |
| 2009/0248021 A1 | 10/2009 | McKenna |
| 2009/0248022 A1 | 10/2009 | Falkenstein et al. |
| 2009/0248050 A1 | 10/2009 | Hirai |
| 2009/0254080 A1 | 10/2009 | Honda |
| 2009/0254081 A1 | 10/2009 | Allison et al. |
| 2009/0261804 A1 | 10/2009 | McKenna et al. |
| 2009/0270771 A1 | 10/2009 | Takahashi |
| 2009/0275865 A1 | 11/2009 | Zhao et al. |
| 2009/0292282 A9 | 11/2009 | Dycus |
| 2009/0299364 A1 | 12/2009 | Batchelor et al. |
| 2009/0312773 A1 | 12/2009 | Cabrera et al. |
| 2009/0318912 A1 | 12/2009 | Mayer et al. |
| 2010/0016857 A1 | 1/2010 | McKenna et al. |
| 2010/0023009 A1 | 1/2010 | Moses et al. |
| 2010/0036375 A1 | 2/2010 | Regadas |
| 2010/0042143 A1 | 2/2010 | Cunningham |
| 2010/0049187 A1 | 2/2010 | Carlton et al. |
| 2010/0049194 A1 | 2/2010 | Hart et al. |
| 2010/0057078 A1 | 3/2010 | Arts et al. |
| 2010/0057081 A1 | 3/2010 | Hanna |
| 2010/0057082 A1 | 3/2010 | Hanna |
| 2010/0057083 A1 | 3/2010 | Hanna |
| 2010/0057084 A1 | 3/2010 | Hanna |
| 2010/0063500 A1 | 3/2010 | Muszala |
| 2010/0069903 A1 | 3/2010 | Allen, IV et al. |
| 2010/0069904 A1 | 3/2010 | Cunningham |
| 2010/0069953 A1 | 3/2010 | Cunningham et al. |
| 2010/0076427 A1 | 3/2010 | Heard |
| 2010/0076430 A1 | 3/2010 | Romero |
| 2010/0076431 A1 | 3/2010 | Allen, IV |
| 2010/0076432 A1 | 3/2010 | Homer |
| 2010/0087816 A1 | 4/2010 | Roy |
| 2010/0094271 A1 | 4/2010 | Ward et al. |
| 2010/0094287 A1 | 4/2010 | Cunningham et al. |
| 2010/0094289 A1 | 4/2010 | Taylor et al. |
| 2010/0100122 A1 | 4/2010 | Hinton |
| 2010/0130971 A1 | 5/2010 | Baily |
| 2010/0130977 A1 | 5/2010 | Garrison et al. |
| 2010/0168741 A1 | 7/2010 | Sanai et al. |
| 2010/0179543 A1 | 7/2010 | Johnson et al. |
| 2010/0179545 A1 | 7/2010 | Twomey et al. |
| 2010/0179546 A1 | 7/2010 | Cunningham |
| 2010/0179547 A1 | 7/2010 | Cunningham et al. |
| 2010/0198218 A1 | 8/2010 | Manzo |
| 2010/0198248 A1 | 8/2010 | Vakharia |
| 2010/0204697 A1 | 8/2010 | Dumbauld et al. |
| 2010/0204698 A1 | 8/2010 | Chapman et al. |
| 2010/0217258 A1 | 8/2010 | Floume et al. |
| 2010/0217264 A1 | 8/2010 | Odom et al. |
| 2010/0228249 A1 | 9/2010 | Mohr et al. |
| 2010/0228250 A1 | 9/2010 | Brogna |
| 2010/0249769 A1 | 9/2010 | Nau, Jr. et al. |
| 2010/0274160 A1 | 10/2010 | Yachi et al. |
| 2010/0274244 A1 | 10/2010 | Heard |
| 2010/0274265 A1 | 10/2010 | Wingardner et al. |
| 2010/0280511 A1 | 11/2010 | Rachlin et al. |
| 2010/0292691 A1 | 11/2010 | Brogna |
| 2010/0305558 A1 | 12/2010 | Kimura et al. |
| 2010/0307934 A1 | 12/2010 | Chowaniec et al. |
| 2010/0312235 A1 | 12/2010 | Bahney |
| 2010/0331742 A1 | 12/2010 | Masuda |
| 2010/0331839 A1 | 12/2010 | Schechter et al. |
| 2011/0004210 A1 | 1/2011 | Johnson et al. |
| 2011/0015632 A1 | 1/2011 | Artale |
| 2011/0018164 A1 | 1/2011 | Sartor et al. |
| 2011/0034918 A1 | 2/2011 | Reschke |
| 2011/0046623 A1 | 2/2011 | Reschke |
| 2011/0054467 A1 | 3/2011 | Mueller et al. |
| 2011/0054468 A1 | 3/2011 | Dycus |
| 2011/0054469 A1 | 3/2011 | Kappus et al. |
| 2011/0054471 A1 | 3/2011 | Gerhardt et al. |
| 2011/0054472 A1 | 3/2011 | Romero |
| 2011/0060333 A1 | 3/2011 | Mueller |
| 2011/0060334 A1 | 3/2011 | Brandt et al. |
| 2011/0060335 A1 | 3/2011 | Harper et al. |
| 2011/0071523 A1 | 3/2011 | Dickhans |
| 2011/0071525 A1 | 3/2011 | Dumbauld et al. |
| 2011/0072638 A1 | 3/2011 | Brandt et al. |
| 2011/0073594 A1 | 3/2011 | Bonn |
| 2011/0077637 A1 | 3/2011 | Brannan |
| 2011/0077648 A1 | 3/2011 | Lee et al. |
| 2011/0077649 A1 | 3/2011 | Kingsley |
| 2011/0082457 A1 | 4/2011 | Kerr et al. |
| 2011/0082494 A1 | 4/2011 | Kerr et al. |
| 2011/0087218 A1* | 4/2011 | Boudreaux ........ A61B 18/1445 606/41 |
| 2011/0087221 A1 | 4/2011 | Siebrecht et al. |
| 2011/0098689 A1 | 4/2011 | Nau, Jr. et al. |
| 2011/0106079 A1 | 5/2011 | Garrison et al. |
| 2011/0118736 A1 | 5/2011 | Harper et al. |
| 2011/0178519 A1 | 7/2011 | Couture et al. |
| 2011/0184405 A1 | 7/2011 | Mueller |
| 2011/0190653 A1 | 8/2011 | Harper et al. |
| 2011/0190765 A1 | 8/2011 | Chojin |
| 2011/0193608 A1 | 8/2011 | Krapohl |
| 2011/0218530 A1 | 9/2011 | Reschke |
| 2011/0230880 A1 | 9/2011 | Chojin et al. |
| 2011/0238066 A1 | 9/2011 | Olson |
| 2011/0238067 A1 | 9/2011 | Moses et al. |
| 2011/0251605 A1 | 10/2011 | Hoarau et al. |
| 2011/0251606 A1 | 10/2011 | Kerr |
| 2011/0251611 A1 | 10/2011 | Horner et al. |
| 2011/0257680 A1 | 10/2011 | Reschke et al. |
| 2011/0257681 A1 | 10/2011 | Reschke et al. |
| 2011/0270245 A1 | 11/2011 | Horner et al. |
| 2011/0270250 A1 | 11/2011 | Horner et al. |
| 2011/0270251 A1 | 11/2011 | Horner et al. |
| 2011/0270252 A1 | 11/2011 | Horner et al. |
| 2011/0276048 A1 | 11/2011 | Kerr et al. |
| 2011/0276049 A1 | 11/2011 | Gerhardt |
| 2011/0295251 A1 | 12/2011 | Garrison |
| 2011/0295313 A1 | 12/2011 | Kerr |
| 2011/0301592 A1 | 12/2011 | Kerr et al. |
| 2011/0301599 A1 | 12/2011 | Roy et al. |
| 2011/0301600 A1 | 12/2011 | Garrison et al. |
| 2011/0301601 A1 | 12/2011 | Garrison et al. |
| 2011/0301602 A1 | 12/2011 | Roy et al. |
| 2011/0301603 A1 | 12/2011 | Kerr et al. |
| 2011/0301604 A1 | 12/2011 | Horner et al. |
| 2011/0301605 A1 | 12/2011 | Homer |
| 2011/0301606 A1 | 12/2011 | Kerr |

(56) References Cited

U.S. PATENT DOCUMENTS

| | | |
|---|---|---|
| 2011/0301637 A1 | 12/2011 | Kerr et al. |
| 2011/0319886 A1 | 12/2011 | Chojin et al. |
| 2011/0319888 A1 | 12/2011 | Mueller et al. |
| 2012/0004658 A1 | 1/2012 | Chojin |
| 2012/0010614 A1 | 1/2012 | Couture |
| 2012/0022532 A1 | 1/2012 | Garrison |
| 2012/0029515 A1 | 2/2012 | Couture |
| 2012/0041438 A1 | 2/2012 | Nau, Jr. et al. |
| 2012/0046659 A1 | 2/2012 | Mueller |
| 2012/0046660 A1 | 2/2012 | Nau, Jr. |
| 2012/0046662 A1 | 2/2012 | Gilbert |
| 2012/0059371 A1 | 3/2012 | Anderson et al. |
| 2012/0059372 A1 | 3/2012 | Johnson |
| 2012/0059374 A1 | 3/2012 | Johnson et al. |
| 2012/0059375 A1 | 3/2012 | Couture et al. |
| 2012/0059408 A1 | 3/2012 | Mueller |
| 2012/0059409 A1 | 3/2012 | Reschke et al. |
| 2012/0078250 A1 | 3/2012 | Orton et al. |
| 2012/0080503 A1* | 4/2012 | Woodard, Jr. ......... A61B 90/92 227/181.1 |
| 2012/0083785 A1 | 4/2012 | Roy et al. |
| 2012/0083786 A1 | 4/2012 | Artale et al. |
| 2012/0083827 A1 | 4/2012 | Artale et al. |
| 2012/0095456 A1 | 4/2012 | Schechter et al. |
| 2012/0095460 A1 | 4/2012 | Rooks et al. |
| 2012/0109187 A1 | 5/2012 | Gerhardt, Jr. et al. |
| 2012/0118507 A1 | 5/2012 | Brandt et al. |
| 2012/0123402 A1 | 5/2012 | Chernov et al. |
| 2012/0123404 A1 | 5/2012 | Craig |
| 2012/0123410 A1 | 5/2012 | Craig |
| 2012/0123413 A1 | 5/2012 | Chernov et al. |
| 2012/0130367 A1 | 5/2012 | Garrison |
| 2012/0136353 A1 | 5/2012 | Romero |
| 2012/0136354 A1 | 5/2012 | Rupp |
| 2012/0143185 A1 | 6/2012 | Nau, Jr. |
| 2012/0165797 A1 | 6/2012 | Cunningham |
| 2012/0165818 A1 | 6/2012 | Odom |
| 2012/0172868 A1 | 7/2012 | Twomey et al. |
| 2012/0172873 A1 | 7/2012 | Artale et al. |
| 2012/0172924 A1 | 7/2012 | Allen, IV |
| 2012/0172925 A1 | 7/2012 | Dumbauld et al. |
| 2012/0184989 A1 | 7/2012 | Twomey |
| 2012/0184990 A1 | 7/2012 | Twomey |
| 2012/0202179 A1 | 8/2012 | Fedotov et al. |
| 2012/0209263 A1 | 8/2012 | Sharp et al. |
| 2012/0215219 A1 | 8/2012 | Roy et al. |
| 2012/0215242 A1 | 8/2012 | Reschke et al. |

FOREIGN PATENT DOCUMENTS

| | | |
|---|---|---|
| CA | 2590520 A1 | 11/2007 |
| CN | 201299462 | 9/2009 |
| DE | 2415263 A1 | 10/1975 |
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 0467501 A1 | 1/1992 |
| EP | 0509670 A3 | 12/1992 |
| EP | 0541930 A1 | 5/1993 |
| EP | 0306123 B1 | 8/1993 |
| EP | 0572131 A1 | 12/1993 |
| EP | 0584787 A1 | 3/1994 |
| EP | 0589555 A1 | 3/1994 |
| EP | 0589453 A3 | 4/1994 |
| EP | 0648475 A1 | 4/1995 |
| EP | 0624348 A3 | 6/1995 |
| EP | 0364216 B1 | 1/1996 |
| EP | 0518230 B1 | 5/1996 |
| EP | 0517243 B1 | 9/1997 |
| EP | 0878169 A1 | 11/1998 |
| EP | 0623316 B1 | 3/1999 |
| EP | 0650701 B1 | 3/1999 |
| EP | 0923907 A1 | 6/1999 |
| EP | 0640317 B1 | 9/1999 |
| EP | 0950378 A1 | 10/1999 |
| EP | 0986990 A1 | 3/2000 |
| EP | 1034747 A1 | 9/2000 |
| EP | 1034748 | 9/2000 |
| EP | 0694290 B1 | 11/2000 |
| EP | 1050278 | 11/2000 |
| EP | 1053719 | 11/2000 |
| EP | 1053720 | 11/2000 |
| EP | 1055399 | 11/2000 |
| EP | 1055400 | 11/2000 |
| EP | 1080694 | 3/2001 |
| EP | 1082944 | 3/2001 |
| EP | 1177771 | 2/2002 |
| EP | 1278007 A1 | 1/2003 |
| EP | 1159926 A3 | 3/2003 |
| EP | 0717966 B1 | 4/2003 |
| EP | 1301135 | 4/2003 |
| EP | 0887046 B1 | 7/2003 |
| EP | 1330991 A1 | 7/2003 |
| EP | 1486177 | 6/2004 |
| EP | 0913126 B1 | 10/2004 |
| EP | 1472984 | 11/2004 |
| EP | 0754437 B2 | 12/2004 |
| EP | 0888747 B1 | 12/2004 |
| EP | 1025807 B1 | 12/2004 |
| EP | 0774232 B1 | 1/2005 |
| EP | 0853922 B1 | 2/2005 |
| EP | 1527747 | 5/2005 |
| EP | 1530952 | 5/2005 |
| EP | 1532932 A1 | 5/2005 |
| EP | 1535581 | 6/2005 |
| EP | 1545360 A1 | 6/2005 |
| EP | 1609430 A1 | 12/2005 |
| EP | 1201192 | 2/2006 |
| EP | 1034746 B1 | 3/2006 |
| EP | 1632192 | 3/2006 |
| EP | 1186274 | 4/2006 |
| EP | 1642543 | 4/2006 |
| EP | 1645238 A1 | 4/2006 |
| EP | 1645240 A2 | 4/2006 |
| EP | 1649821 | 4/2006 |
| EP | 0875209 B1 | 5/2006 |
| EP | 1685806 A2 | 8/2006 |
| EP | 1707143 A1 | 10/2006 |
| EP | 1767163 A1 | 3/2007 |
| EP | 1767164 | 3/2007 |
| EP | 1769765 A1 | 4/2007 |
| EP | 1769766 | 4/2007 |
| EP | 1772109 | 4/2007 |
| EP | 1785097 | 5/2007 |
| EP | 1785098 | 5/2007 |
| EP | 1785101 | 5/2007 |
| EP | 1787597 | 5/2007 |
| EP | 1810625 A1 | 7/2007 |
| EP | 1810628 A1 | 7/2007 |
| EP | 1842500 | 10/2007 |
| EP | 1878400 | 1/2008 |
| EP | 1894535 | 3/2008 |

(56) References Cited

FOREIGN PATENT DOCUMENTS

| | | |
|---|---|---|
| EP | 1929970 | 6/2008 |
| EP | 1946715 | 7/2008 |
| EP | 1958583 A2 | 8/2008 |
| EP | 1990019 | 11/2008 |
| EP | 1994904 | 11/2008 |
| EP | 1683496 | 12/2008 |
| EP | 1997438 | 12/2008 |
| EP | 1997439 | 12/2008 |
| EP | 1527744 | 2/2009 |
| EP | 2103268 | 9/2009 |
| EP | 2105104 | 9/2009 |
| EP | 2147649 | 1/2010 |
| EP | 2153791 | 2/2010 |
| EP | 2206474 | 7/2010 |
| EP | 1920725 | 10/2010 |
| EP | 2243439 | 10/2010 |
| EP | 2294998 | 3/2011 |
| EP | 2301467 | 3/2011 |
| EP | 1628586 | 7/2011 |
| GB | 623316 | 5/1949 |
| GB | 1490585 | 11/1977 |
| GB | 2213416 A | 8/1989 |
| GB | 2214430 A | 9/1989 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 9-122138 A | 5/1997 |
| JP | 0010000195 A | 1/1998 |
| JP | 10-155798 A | 6/1998 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000342599 A | 12/2000 |
| JP | 2000350732 A | 12/2000 |
| JP | 2001-8944 | 1/2001 |
| JP | 2001-29356 | 2/2001 |
| JP | 2001128990 A | 5/2001 |
| JP | 2001-190564 A | 7/2001 |
| JP | 2001-3400 | 11/2001 |
| JP | 2002-136525 A | 5/2002 |
| JP | 2002-528166 A | 9/2002 |
| JP | 2003-175052 A | 6/2003 |
| JP | 2003245285 A | 9/2003 |
| JP | 2004-517668 A | 6/2004 |
| JP | 2004-528869 A | 9/2004 |
| JP | 2005-253789 A | 9/2005 |
| JP | 2006-015078 A | 1/2006 |
| JP | 2006-501939 A | 1/2006 |
| JP | 2006-095316 A | 4/2006 |
| JP | 2011125195 A | 6/2011 |
| SU | 401367 A1 | 10/1973 |
| WO | 89/00757 | 1/1989 |
| WO | 92/04873 | 4/1992 |
| WO | 92/06642 | 4/1992 |
| WO | 93/19681 | 10/1993 |
| WO | 93/21845 | 11/1993 |
| WO | 94/00059 A1 | 1/1994 |
| WO | 94/08524 | 4/1994 |
| WO | 94/20025 | 9/1994 |
| WO | 95/02369 | 1/1995 |
| WO | 95/07662 | 3/1995 |
| WO | 95/15124 | 6/1995 |
| WO | 95/20360 | 8/1995 |
| WO | 95/20921 | 8/1995 |
| WO | 96/05776 | 2/1996 |
| WO | 96/11635 | 4/1996 |
| WO | 96-22056 A1 | 7/1996 |
| WO | 96/13218 | 9/1996 |
| WO | 97/00646 | 1/1997 |
| WO | 97/00647 | 1/1997 |
| WO | 97/10764 | 3/1997 |
| WO | 97/18768 | 5/1997 |
| WO | 97/24073 | 7/1997 |
| WO | 97/24993 | 7/1997 |
| WO | 98/14124 | 4/1998 |
| WO | 98/27880 | 7/1998 |
| WO | 98/31290 | 7/1998 |
| WO | 98/43264 | 10/1998 |
| WO | 99/03407 | 1/1999 |
| WO | 99/03408 | 1/1999 |
| WO | 99/03409 | 1/1999 |
| WO | 99/03414 | 1/1999 |
| WO | 99/12488 | 3/1999 |
| WO | 99-23933 A2 | 5/1999 |
| WO | 99/23959 | 5/1999 |
| WO | 99-25261 A1 | 5/1999 |
| WO | 99/40857 | 8/1999 |
| WO | 99/40861 | 8/1999 |
| WO | 99/51158 | 10/1999 |
| WO | 99/66850 | 12/1999 |
| WO | 00/24322 | 5/2000 |
| WO | 00/24330 | 5/2000 |
| WO | 00/24331 | 5/2000 |
| WO | 00/33753 | 6/2000 |
| WO | 0036986 A1 | 6/2000 |
| WO | 00/41638 | 7/2000 |
| WO | 00/47124 | 8/2000 |
| WO | 00/53112 | 9/2000 |
| WO | 0059392 A1 | 10/2000 |
| WO | 01/01847 A1 | 1/2001 |
| WO | 0100114 A1 | 1/2001 |
| WO | 01/17448 | 3/2001 |
| WO | 0115614 A1 | 3/2001 |
| WO | 0154604 A1 | 8/2001 |
| WO | 01/66025 | 9/2001 |
| WO | 02/07627 | 1/2002 |
| WO | 02/45589 A2 | 6/2002 |
| WO | 02/058544 | 8/2002 |
| WO | 02/067798 | 9/2002 |
| WO | 02/080783 | 10/2002 |
| WO | 02/080784 | 10/2002 |
| WO | 02/080785 | 10/2002 |
| WO | 02/080786 | 10/2002 |
| WO | 02/080793 | 10/2002 |
| WO | 02/080794 | 10/2002 |
| WO | 02/080795 | 10/2002 |
| WO | 02/080796 | 10/2002 |
| WO | 02/080797 | 10/2002 |
| WO | 02/080798 | 10/2002 |
| WO | 02/080799 A1 | 10/2002 |
| WO | 02/081170 | 10/2002 |
| WO | 02/085218 A2 | 10/2002 |
| WO | 02/094746 A1 | 11/2002 |
| WO | 03/061500 | 7/2003 |
| WO | 03/068046 A2 | 8/2003 |
| WO | 03/096880 A2 | 11/2003 |
| WO | 03/101311 | 12/2003 |
| WO | 03/090630 A3 | 4/2004 |
| WO | 2004-028585 A2 | 4/2004 |
| WO | 2004/032776 A1 | 4/2004 |
| WO | 2004/032777 A1 | 4/2004 |
| WO | 2004/052221 A1 | 6/2004 |
| WO | 2004/073488 A2 | 9/2004 |
| WO | 2004/073490 A2 | 9/2004 |
| WO | 2004/073753 A2 | 9/2004 |
| WO | 2004/082495 A1 | 9/2004 |
| WO | 2004083797 A2 | 9/2004 |

(56) References Cited

FOREIGN PATENT DOCUMENTS

| WO | 2004/098383 A2 | 11/2004 |
|---|---|---|
| WO | 2004/103156 A2 | 12/2004 |
| WO | 2005/004734 A1 | 1/2005 |
| WO | 2005/004735 A1 | 1/2005 |
| WO | 2005-009255 A1 | 2/2005 |
| WO | 2005/011049 A2 | 2/2005 |
| WO | 2005/030071 A1 | 4/2005 |
| WO | 2005/048809 A1 | 6/2005 |
| WO | 2005/050151 A1 | 6/2005 |
| WO | 2005/110264 A2 | 11/2005 |
| WO | 2006021269 A1 | 3/2006 |
| WO | 2008/008457 A2 | 1/2008 |
| WO | 2008/045348 A2 | 4/2008 |
| WO | 2008/045350 A2 | 4/2008 |
| WO | 2008040483 A1 | 4/2008 |
| WO | 2008-112147 A1 | 9/2008 |
| WO | 2009-005850 A1 | 1/2009 |
| WO | 2009/039510 A1 | 3/2009 |
| WO | 2009032623 A2 | 3/2009 |
| WO | 2009039179 A1 | 3/2009 |
| WO | 200124097 A1 | 10/2009 |
| WO | 2010104753 A1 | 9/2010 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed 6/920/00, Thomas P. Ryan.
U.S. Appl. No. 12/336,970, filed Dec. 17, 2008, Paul R. Sremeich.
U.S. Appl. No. 13/050,182, filed Mar. 17, 2011, Glenn a. Homer.
U.S. Appl. No. 13/072,945, filed Mar. 28, 2011, Patrick L. Dumbauld.
U.S. Appl. No. 13/080,383, filed Apr. 5, 2011, David M. Garrison.
U.S. Appl. No. 13/085,144, filed Apr. 12, 2011, Keir Hart.
U.S. Appl. No. 13/091,331, filed Apr. 21, 2011, Jeffrey R. Townsend.
U.S. Appl. No. 13/102,573, filed May 6, 2011, John R. Twomey.
U.S. Appl. No. 13/102,604, filed May 6, 2011, Paul E. Ourada.
U.S. Appl. No. 13/108,093, filed May 16, 2011, Boris Chernov.
U.S. Appl. No. 13/108,129, filed May 16, 2011, Boris Chernov.
U.S. Appl. No. 13/108,152, filed May 16, 2011, Boris Chernov.
U.S. Appl. No. 13/108,177, filed May 16, 2011, Boris Chernov.
U.S. Appl. No. 13/108,196, filed May 16, 2011, Boris Chernov.
U.S. Appl. No. 13/108,441, filed May 16, 2011, Boris Chernov.
U.S. Appl. No. 13/108,468, filed May 16, 2011, Boris Chernov.
U.S. Appl. No. 13/111,642, filed May 19, 2011, John R. Twomey.
U.S. Appl. No. 13/111,678, filed May 19, 2011, Nikolay Kharin.
U.S. Appl. No. 13/113,231, filed May 23, 2011, David M. Garrison.
U.S. Appl. No. 13/157,047, filed Jun. 9, 2011, John R. Twomey.
U.S. Appl. No. 13/162,814, filed Jun. 17, 2011, Barbara R. Tyrrell.
U.S. Appl. No. 13/166,477, filed Jun. 22, 2011, Daniel A. Joseph.
U.S. Appl. No. 13/166,497, filed Jun. 22, 2011, Daniel A. Joseph.
U.S. Appl. No. 13/179,919, filed Jul. 11, 2011, Russell D. Hempstead.
U.S. Appl. No. 13/179,960, filed Jul. 11, 2011, Boris Chernov.
U.S. Appl. No. 13/179,975, filed Jul. 11, 2011, Grant T. Sims.
U.S. Appl. No. 13/180,018, filed Jul. 11, 2011, Chase Collings.
U.S. Appl. No. 13/183,856, filed Jul. 15, 2011, John R. Twomey.
U.S. Appl. No. 13/185,593, filed Jul. 19, 2011, James D. Allen, IV.
U.S. Appl. No. 13/204,841, filed Aug. 8, 2011, Edward J. Chojin.
U.S. Appl. No. 13/205,999, filed Aug. 9, 2011, Jeffrey R. Unger.
U.S. Appl. No. 13/212,297, filed Aug. 18, 2011, Allan J. Evans.
U.S. Appl. No. 13/212,308, filed Aug. 18, 2011, Allan J. Evans.
U.S. Appl. No. 13/212,329, filed Aug. 18, 2011, Allan J. Evans.
U.S. Appl. No. 13/212,343, filed Aug. 18, 2011, Duane E. Kerr.
U.S. Appl. No. 13/223,521, filed Sep. 1, 2011, John R. Twomey.
U.S. Appl. No. 13/227,220, filed Sep. 7, 2011, James D. Allen, IV.
U.S. Appl. No. 13/228,742, filed Sep. 9, 2011, Duane E. Kerr.
U.S. Appl. No. 13/231,643, filed Sep. 13, 2011, Keir Hart.
U.S. Appl. No. 13/234,357, filed Sep. 16, 2011, James D. Allen, IV.
U.S. Appl. No. 13/236,168, filed Sep. 19, 2011, James D. Allen, IV.
U.S. Appl. No. 13/236,271, filed Sep. 19, 2011, Monte S. Fry.
U.S. Appl. No. 13/243,628, filed Sep. 23, 2011, William Ross Whitney.
U.S. Appl. No. 13/247,778, filed Sep. 28, 2011, John R. Twomey.
U.S. Appl. No. 13/247,795, filed Sep. 28, 2011, John R. Twomey.
U.S. Appl. No. 13/248,976, filed Sep. 29, 2011, James D. Allen, IV.
U.S. Appl. No. 13/249,013, filed Sep. 29, 2011, Jeffrey R. Unger.
Extended European Search Report corresponding to counterpart Int'l Appln. No. EP 12 15 1071.3 dated Mar. 23, 2017.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020528.9 dated Aug. 4, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 015215.8 dated Feb. 24, 2010.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 157500.9 dated Jul. 30, 2010.
Int'l Search Report EP 10 159205.3 dated Jul. 7, 2010.
Int'l Search Report EP 10 160870.1 dated Aug. 9, 2010.
Int'l Search Report EP 10 161596.1 dated Jul. 28, 2010.
Int'l Search Report EP 10 167655.9 dated Aug. 31, 2011.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175559.3 dated May 25, 2012.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182019.9 dated Aug. 22, 2011.
Int'l Search Report EP 10 182022.3 dated Mar. 11, 2011.
Int'l Search Report EP 10 185386.9 dated Jan. 10, 2011.
Int'l Search Report EP 10 185405.7 dated Jan. 5, 2011.
Int'l Search Report EP 10 186527.7 dated Jun. 17, 2011.
Int'l Search Report EP 10 189206.5 dated Mar. 17, 2011.
Int'l Search Report EP 10 191320.0 dated Feb. 15, 2011.
Int'l Search Report EP 11 006233.8 dated Feb. 2, 2012.
Int'l Search Report EP 11 007972.0 dated Dec. 28, 2011.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05004431.2 dated Jun. 2, 2005.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.

(56) References Cited

OTHER PUBLICATIONS

Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 016911.5 extended dated Mar. 2, 2011.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.

W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Venous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.

(56) References Cited

OTHER PUBLICATIONS

McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
U.S. Appl. No. 13/249,024, filed Sep. 29, 2011, John R. Twomey.
U.S. Appl. No. 13/251,380, filed Oct. 3, 2011, Duane E. Kerr.
U.S. Appl. No. 13/277,373, filed Oct. 20, 2011, Glenn A. Homer.
U.S. Appl. No. 13/277,926, filed Oct. 20, 2011, David M. Garrison.
U.S. Appl. No. 13/277,962, filed Oct. 20, 2011, David M. Garrison.
U.S. Appl. No. 13/293,754, filed Nov. 10, 2011, Jeffrey M. Roy.
U.S. Appl. No. 13/306,523, filed Nov. 29, 2011, David M. Garrison.
U.S. Appl. No. 13/306,553, filed Nov. 29, 2011, Duane E. Kerr.
U.S. Appl. No. 13/308,104, filed Nov. 30, 2011, John R. Twomey.
U.S. Appl. No. 13/312,172, filed Dec. 6, 2011, Robert J. Behnke, II.
U.S. Appl. No. 13/324,863, filed Dec. 13, 2011, William H. Nau, Jr.
U.S. Appl. No. 13/344,729, filed Jan. 6, 2012, James D. Allen, IV.
U.S. Appl. No. 13/355,829, filed Jan. 23, 2012, John R.Twomey.
U.S. Appl. No. 13/357,979, filed Jan. 25, 2012, David M. Garrison.
U.S. Appl. No. 13/358,136, filed Jan. 25, 2012, James D. Allen, IV.
U.S. Appl. No. 13/360,925, filed Jan. 30, 2012, James H. Orszulak.
U.S. Appl. No. 13/400,290, filed Feb. 20, 2012, Eric R. Larson.
U.S. Appl. No. 13/404,435, filed Feb. 24, 2012, Kim V. Brandt.
U.S. Appl. No. 13/404,476, filed Feb. 24, 2012, Kim V. Brandt.
U.S. Appl. No. 13/412,879, filed Mar. 6, 2012, David M. Garrison.
U.S. Appl. No. 13/412,897, filed Mar. 6, 2012, Joanna Ackley.
U.S. Appl. No. 13/421,373, filed Mar. 15, 2012, John R. Twomey.
U.S. Appl. No. 13/430,325, filed Mar. 26, 2012, William H. Nau, Jr.
U.S. Appl. No. 13/433,924, filed Mar. 29, 2012, Keir Hart.
U.S. Appl. No. 13/448,577, filed Apr. 17, 2012, David M. Garrison.
U.S. Appl. No. 13/460,455, filed Apr. 30, 2012, Luke Waaler.
U.S. Appl. No. 13/461,335, filed May 1, 2012, James D. Allen, IV.
U.S. Appl. No. 13/461,378, filed May 1, 2012, James D. Allen, IV.
U.S. Appl. No. 13/461,397, filed May 1, 2012, James R. Unger.
U.S. Appl. No. 13/461,410, filed May 1, 2012, James R. Twomey.
U.S. Appl. No. 13/464,569, filed May 4, 2012, Duane E. Kerr.
U.S. Appl. No. 13/466,274, filed May 8, 2012, Stephen M. Kendrick.
U.S. Appl. No. 13/467,767, filed May 9, 2012, Duane E. Kerr.
U.S. Appl. No. 13/470,543, filed May 14, 2012, Sean T. Dycus.
U.S. Appl. No. 13/470,775, filed May 14, 2012, James D. Allen, IV.
U.S. Appl. No. 13/470,797, filed May 14, 2012, John J. Kappus.
U.S. Appl. No. 13/482,589, filed May 29, 2012, Eric R. Larson.
U.S. Appl. No. 13/483,733, filed May 30, 2012, Dennis W. Butcher.
U.S. Appl. No. 13/488,093, filed Jun. 4, 2012, Kristin D. Johnson.
U.S. Appl. No. 13/491,853, filed Jun. 8, 2012, Jessica E. Olson.
U.S. Appl. No. 13/537,517, filed Jun. 29, 2012, David N. Heard.
U.S. Appl. No. 13/537,577, filed Jun. 29, 2012, Tony Moua.
U.S. Appl. No. 13/550,322, filed Jul. 16, 2012, John J. Kappus.
U.S. Appl. No. 13/571,055, filed Aug. 9, 2012, Paul Guerra.
U.S. Appl. No. 13/571,821, filed Aug. 10, 2012, Joseph D. Bucciaglia.
U.S. Appl. No. 13/584,194, filed Aug. 13, 2012, Sean T. Dycus.

Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal Feb. 6, 1976, vol. 1, nr. 5431 p. 361, ISSN: 0007-1447.
Carbonell et al., "Comparison of the Gyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte,NC; Date: Aug. 2003.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 153503.5 dated Mar. 5, 2012.
Int'l Search Report EP 11 159771.2 dated May 28, 2010.
Int'l Search Report EP 11 161117.4 dated Jun. 30, 2011.
Int'l Search Report EP 11 161118.2 dated Oct. 12, 2011.
Int'l Search Report EP 11 164274.0 dated Aug. 3, 2011.
Int'l Search Report EP 11 164275.7 dated Aug. 25, 2011.
Int'l Search Report EP 11 167437.0 dated Aug. 8, 2011.
Int'l Search Report EP 11 168419.7 dated Oct. 20, 2011.
Int'l Search Report EP 11 168458.5 dated Jul. 29, 2011.
Int'l Search Report EP 11 173008.1 dated Nov. 4, 2011.
Int'l Search Report EP 11 179514 dated Nov. 4, 2011.
Int'l Search Report EP 11 180182.5 dated Nov. 15, 2011.
Int'l Search Report EP 11 180183 dated Nov. 30, 2011.
Int'l Search Report EP 11 183265.5 dated Nov. 28, 2011.
Int'l Search Report EP 11 183476.8 dated Jan. 18, 2012.
Int'l Search Report EP 11 185028.5 dated Jan. 2, 2012.
Int'l Search Report EP 11 189521.5 dated Feb. 20, 2012.
Int'l Search Report EP 11 190723.4 dated Mar. 16, 2012.
Int'l Search Report EP 12 155726.8 dated May 25, 2012.
Int'l Search Report EP 12 155728.4 dated Jul. 4, 2012.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US03/28539 dated Jan. 6, 2004.
Int'l Search Report PCT/US04/03436 dated Mar. 3, 2005.
Int'l Search Report PCT/US04/13273 dated Dec. 15, 2004.
Int'l Search Report PCT/US04/15311dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.

* cited by examiner

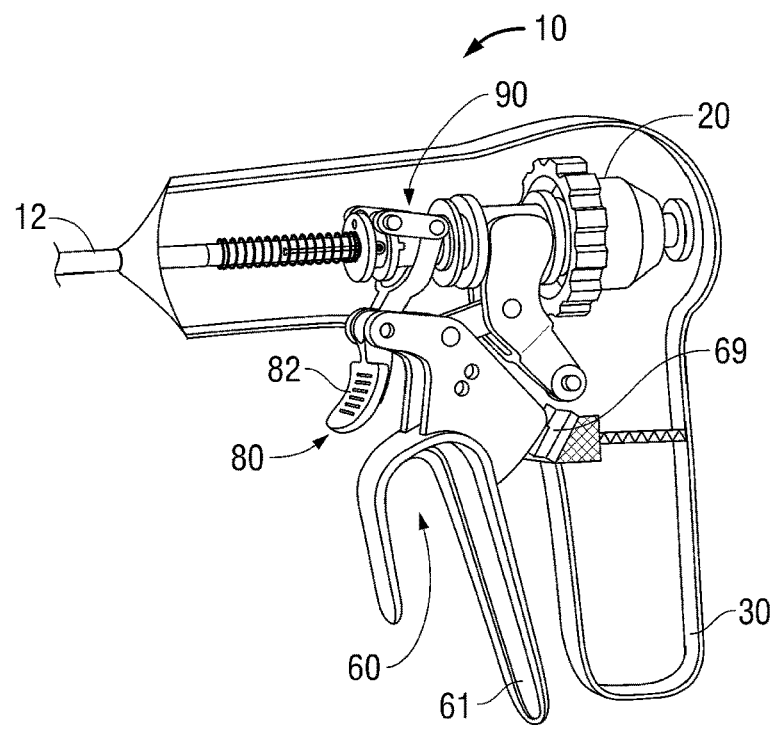
FIG. 7
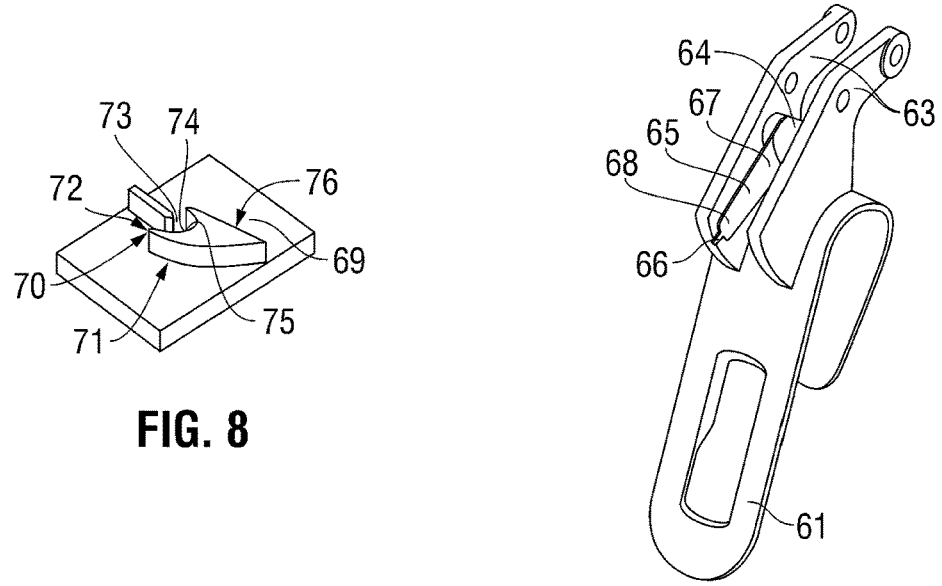
FIG. 8
FIG. 9

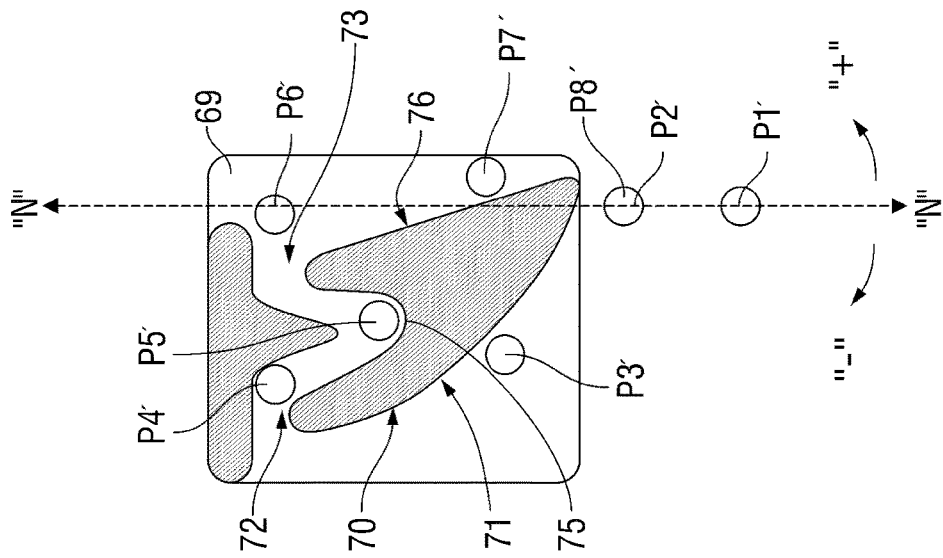
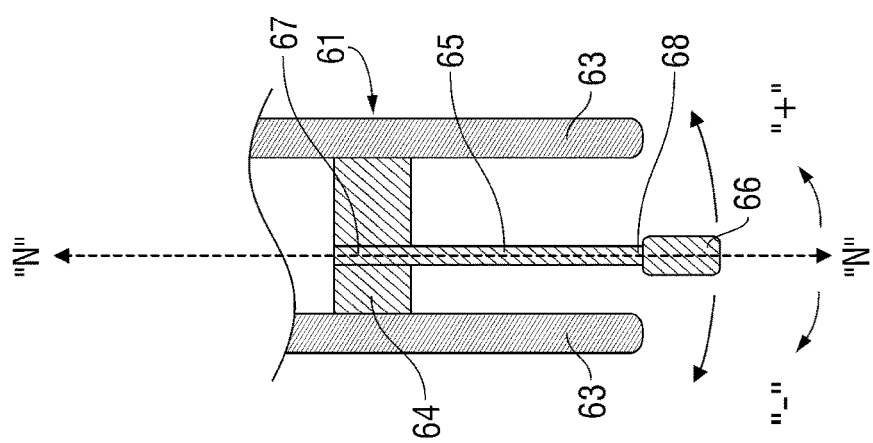

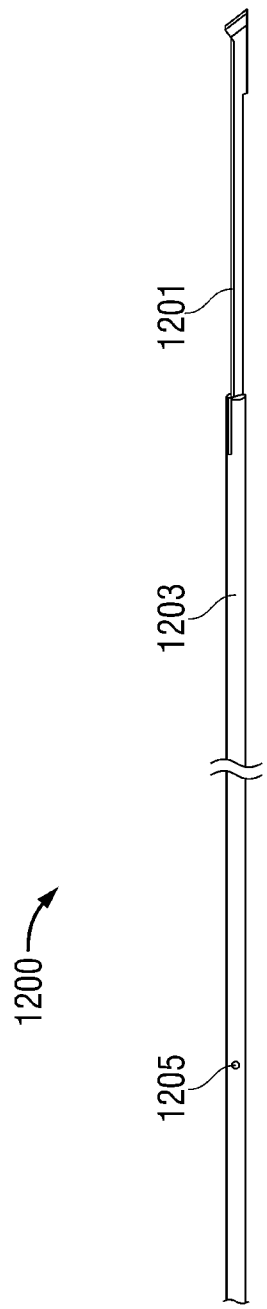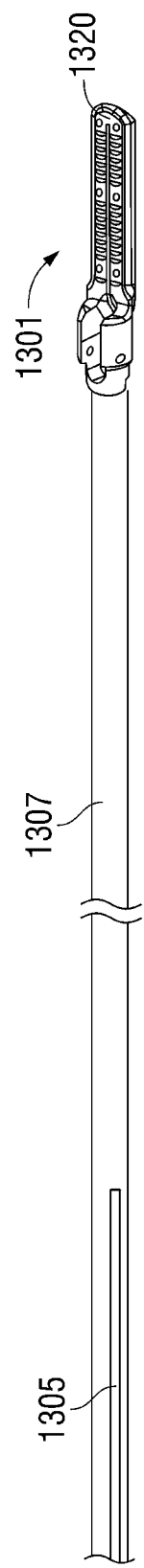
FIG. 12
FIG. 13

TRIGGER LOCKOUT AND KICKBACK MECHANISM FOR SURGICAL INSTRUMENTS

CROSS-REFERENCE TO RELATED APPLICATIONS

This application is a continuation of U.S. patent application Ser. No. 13/401,964, filed Feb. 22, 2012, which is a continuation-in-part of U.S. patent application Ser. No. 13/006,538, filed Jan. 14, 2011, now U.S. Pat. No. 8,945,175, the entire contents of each of which is incorporated by reference herein.

BACKGROUND

Technical Field

The present disclosure relates to surgical instruments. More particularly, the present disclosure relates to a trigger lockout and kickback mechanism for use with surgical instruments.

Background of Related Art

Electrosurgical instruments, e.g., forceps, utilize both mechanical clamping action and electrical energy to effect hemostasis by heating tissue and blood vessels to coagulate, cauterize and/or seal tissue. As an alternative to open forceps for use with open surgical procedures, many modern surgeons use endoscopic or laparoscopic instruments for remotely accessing organs through smaller, puncture-like incisions or natural orifices. As a direct result thereof, patients tend to benefit from less scarring and reduced healing time.

Many endoscopic surgical procedures require cutting or ligating blood vessels or vascular tissue. Due to the inherent spatial considerations of the surgical cavity, surgeons often have difficulty suturing vessels or performing other traditional methods of controlling bleeding, e.g., clamping and/or tying-off transected blood vessels. By utilizing an endoscopic electrosurgical forceps, a surgeon can either cauterize, coagulate/desiccate and/or simply reduce or slow bleeding simply by controlling the intensity, frequency and duration of the electrosurgical energy applied through the jaw members to the tissue. Most small blood vessels, i.e., in the range below two millimeters in diameter, can often be closed using standard electrosurgical instruments and techniques. However, if a larger vessel is ligated, it may be necessary for the surgeon to convert the endoscopic procedure into an open-surgical procedure and thereby abandon the benefits of endoscopic surgery. Alternatively, the surgeon can seal the larger vessel or tissue. Typically, after a vessel or tissue is sealed, the surgeon advances a knife to sever the sealed tissue disposed between the opposing jaw members.

SUMMARY

As used herein, the term "distal" refers to the portion that is being described which is further from a user, while the term "proximal" refers to the portion that is being described which is closer to a user.

In accordance with at least one aspect of the present disclosure, a forceps includes an end effector assembly including first and second jaw members, at least one of the jaw members movable relative to the other between an open position and a closed position for grasping tissue therebetween. The forceps further includes a blade movable between a retracted position wherein the blade is proximal to the jaw members and a deployed position wherein the blade extends at least partially between the jaw members to cut tissue grasped therebetween, a lever member movable between an initial position and a compressed position to move the jaw members between the open and closed positions, and a trigger member operably coupled to the blade and positionable to move the blade between the retracted position and the deployed position, the trigger member defining an actuation path therealong. The forceps also include a trigger safety member pivotably coupled to the lever member such that, when the lever member is disposed in the initial position, the trigger safety member is disposed in a position, blocking actuation of the trigger member and when the lever member is disposed in the compressed position, the trigger safety member is disposed in a position wherein the trigger safety member is displaced from the actuation path to permit movement of the trigger member, wherein the safety member rotates relative to the lever member as a function of movement of the lever member to block/unblock the trigger member.

In accordance with another aspect of the present disclosure, the forceps further include a housing enclosing at least a portion of the lever member, the trigger member, and the trigger safety member.

In accordance with yet another aspect of the present disclosure, the lever member is operably coupled to the housing at a pivot and the trigger member is operably coupled to the housing at a different pivot.

In accordance with yet another aspect of the present disclosure, the lever member and the trigger member are operably coupled to the housing at a single pivot.

In accordance with another aspect of the present disclosure, the forceps further include at least one blade deployment member operably coupled to the blade at an engagement pin and to the trigger member about a pivot.

In accordance with another aspect of the present disclosure, the forceps further include a drive assembly operably coupled to at least one of the first and second jaw members and positionable to actuate the jaw members between the open position and the closed position.

In accordance with another aspect of the present disclosure, the forceps further include at least one driving member operably coupled to the housing, to the trigger safety member, and to the drive assembly at a driving end.

In accordance with yet another aspect of the present disclosure, the lever member is operably coupled to trigger safety member about a trigger pivot.

In accordance with another aspect of the present disclosure, the forceps further include a latch mechanism configured to releasably secure the lever member in the compressed position.

In accordance with yet another aspect of the present disclosure, the trigger safety member is further configured to kickback and forcibly return the trigger member to an un-actuated position.

In accordance with another aspect of the present disclosure, the forceps further include a spring to bias the trigger member towards an un-actuated position.

In accordance with another aspect of the present disclosure, a forceps include a housing and an end effector assembly including first and second jaw members, at least one of the jaw members movable relative to the other between an open position and a closed position for grasping tissue there between. The forceps further have a blade, the blade movable between a retracted position wherein the blade is proximal to the jaw members and a deployed position wherein the blade extends at least partially between the jaw members to cut tissue grasped therebetween, and a lever member coupled to the housing and to the end effector assembly and movable between an initial position and a compressed position to move the jaw members between the open position and the closed position. The forceps further have a trigger member operably coupled to the housing and coupled to the blade via a blade deployment member, wherein the blade deployment member is operably coupled to the blade at an engagement pin, wherein the trigger member is positionable to move the blade between the retracted position and the deployed position, the trigger member defining an actuation path therealong, a drive assembly operably coupled to at least one of the first and second jaw members to actuate the jaw members between the open position and the closed position, and at least one driving member operably coupled to the housing at a point, to the trigger safety member a different point, and to the drive assembly at a driving end. The forceps also have a trigger safety member pivotably coupled to the lever member such that, when the lever member is disposed in the initial position, the trigger safety member is disposed in a position blocking actuation of the trigger member, and when the lever member is disposed in the compressed position, the trigger safety member is disposed in a position wherein the trigger safety member is displaced from the actuation path to permit movement of the trigger member, wherein the safety member rotates relative to the lever member as a function of movement of the lever member to block/unblock the trigger member.

In accordance with another aspect of the present disclosure, the forceps further include a latch mechanism configured to releasably secure the lever member in the compressed position.

In accordance with another aspect of the present disclosure, the trigger safety member is further configured to kickback and forcibly return the trigger member to an un-actuated position.

In accordance with another aspect of the present disclosure, the forceps further include a spring to bias the trigger member towards an un-actuated position.

BRIEF DESCRIPTION OF THE DRAWINGS

Various aspects of the present disclosure are described herein with reference to the drawings, wherein like reference numerals identify similar or identical elements:

FIG. 7 is a perspective view of the handle assembly of the forceps of FIG. 1A wherein a portion of the housing has been removed to show the internal components therein, the handle assembly including another aspect of a latch mechanism disposed in an actuated position;

FIG. 8 is a isolated, perspective view of a pin track member and cantilever spring of the latch mechanism of FIG. 7;

FIG. 9 is an isolated, perspective view of a lever of the latch mechanism of FIG. 7;

FIG. 10 is a transverse, cross-sectional view of the lever of FIG. 9;

FIG. 11 is a schematic illustration of the use of the latch mechanism of FIG. 7;

FIG. 12 is a perspective view of a blade in accordance with an aspect of the present disclosure and configured for use with the forceps of FIG. 1A;

FIG. 13 is a perspective view of a shaft and a portion of an end effector assembly configured for use with the forceps of FIG. 1A;

DETAILED DESCRIPTION

Figure 1A:
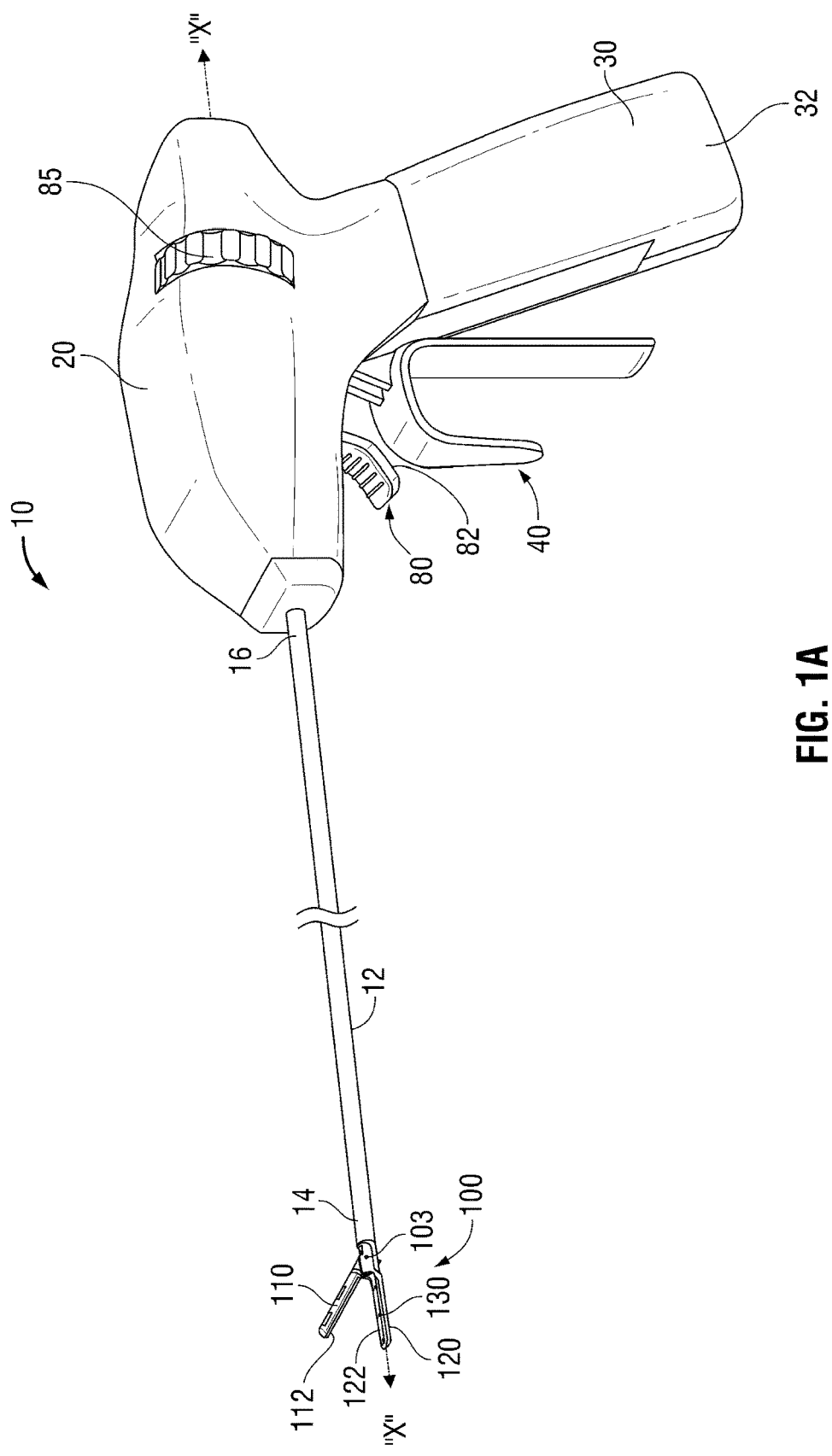
FIG. 1A is a perspective view of a forceps including an end effector assembly in accordance with an aspect of the present disclosure wherein jaw members of the end effector assembly are disposed in a spaced-apart position.
Figure 1B:
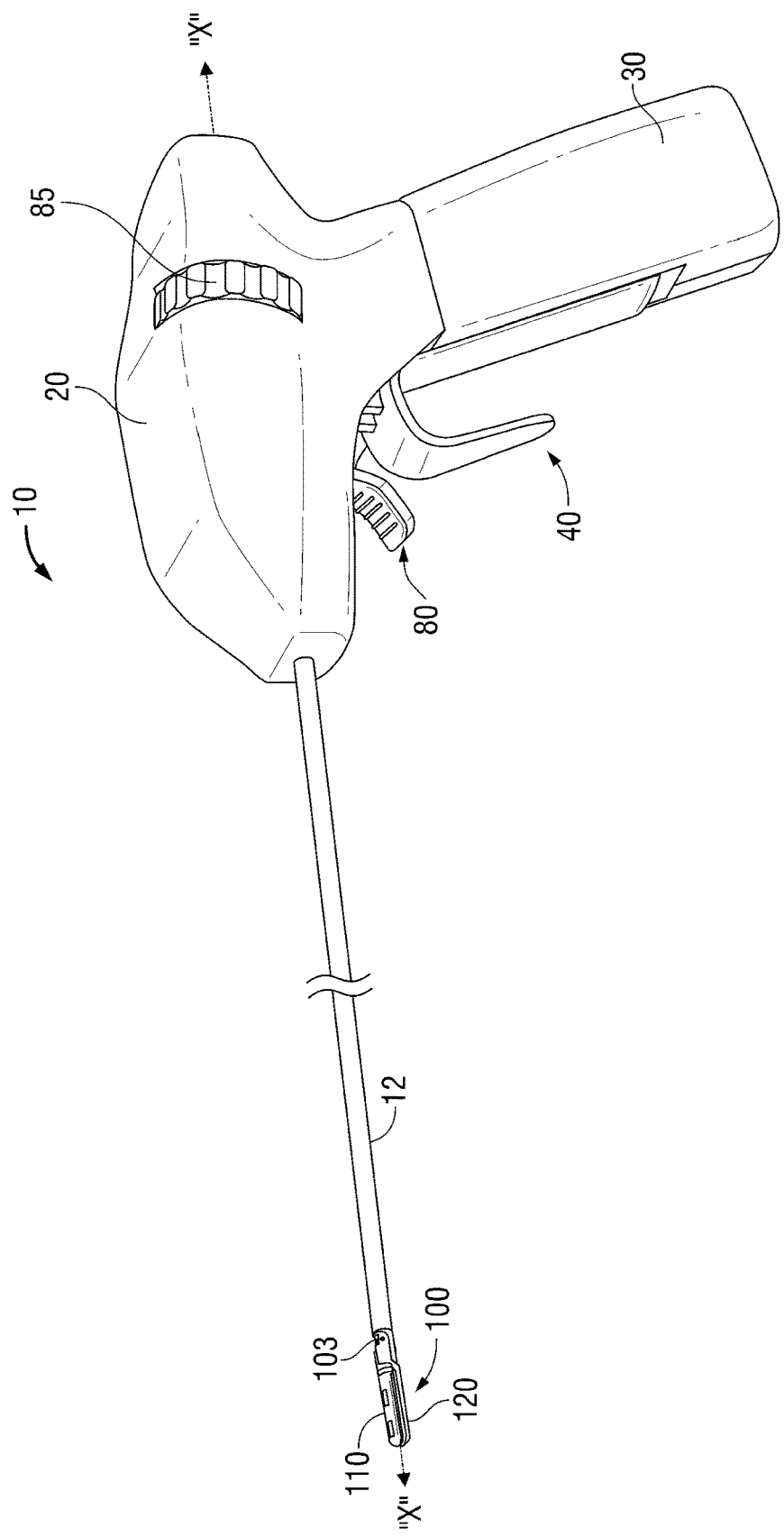
FIG. 1B is a perspective view of the forceps of FIG. 1A wherein the jaw members of the end effector assembly are disposed in an approximated position.

Turning now to FIGS. 1A and 1B, forceps 10 is one example of an instrument for use in accordance with the present disclosure. Forceps 10 including a housing 20, a handle assembly 30, a lever latch assembly 40, a trigger assembly 80, a rotating assembly 85, and an end effector assembly 100. Forceps 10 further includes a shaft 12 having a distal end 14 configured to mechanically engage end effector assembly 100 and a proximal end 16 that mechanically engages housing 20. Alternatively, any surgical instrument having a lever latch assembly operable to control one or more functions of the end effector assembly may be provided.

With continued reference to FIGS. 1A and 1B, end effector assembly 100 includes a pair of opposing jaw members 110 and 120. End effector assembly 100 is designed as a unilateral assembly, i.e., jaw member 120 is fixed relative to the shaft 12 and jaw member 110 is moveable about a pivot 103 relative to jaw member 120. However, either, or both jaw members 110, 120 may be moveable with respect to the other. In either embodiment, jaw members 110, 120 are moveable from a spaced-apart position, as shown in FIG. 1A, to an approximated position, as shown in FIG. 1B, to grasp tissue therebetween. Further, one or both of jaw members 110, 120 may include an electrically conductive tissue sealing surface 112, 122, respectively. Sealing surfaces 112, 122 are disposed in opposed relation relative to one another such that, with jaw members 110, 120 in the approximated position grasping tissue therebetween, electrosurgical energy may be supplied to one or both of sealing surfaces 112, 122 of jaw members 110, 120, respectively, to seal tissue grasped therebetween.

One or both of jaw members 110, 120 may also include a longitudinally extending blade channel 130 to permit reciprocation of a blade (not shown) therethrough for dividing tissue grasped therebetween. Trigger assembly 80 is operably coupled to the blade (not shown) such that, upon actuation of trigger 82, the blade (not shown) is translated from a retracted position to an extended position wherein the blade (not shown) is advanced between jaw members 110, 120 to cut tissue grasped therebetween. Further, trigger 82 may be biased toward an un-actuated position such that, upon release of trigger 82, the blade (not shown) is returned to the retracted position.

Rotating assembly 85 is integrally associated with housing 20 and is rotatable in either direction about a longitudinal axis "X-X" to rotate jaw members 110, 120 with respect to housing 20 about longitudinal axis "X-X."

Handle assembly 30 extends downwardly from housing 20 and is releasably engageable with housing 20. Handle assembly 30 is ergonomically configured such that, when engaged with housing 20, a surgeon may grasp handle assembly 30 and operate lever latch assembly 40, trigger assembly 80 and/or rotating assembly 85 with a single hand. Handle assembly 30 further includes a battery pack (not shown) disposed within a battery housing 32. The battery pack (not shown) of handle assembly 30 provides power to forceps 10, e.g., for energizing sealing surfaces 112, 122 of jaw members 110, 120, respectively. More particularly, the battery pack (not shown) is configured to electrically couple to a generator (not shown) disposed within housing 20 for powering the generator (not shown). The generator (not shown), in turn, supplies the desired energy to sealing surfaces 112, 122 of jaw members 110, 120, respectively, of end effector assembly 100. Alternatively, forceps 10 may be configured to be coupled to an external power source (not shown) and/or generator (not shown), e.g., via an electrosurgical cable (not shown).

Figure 2:
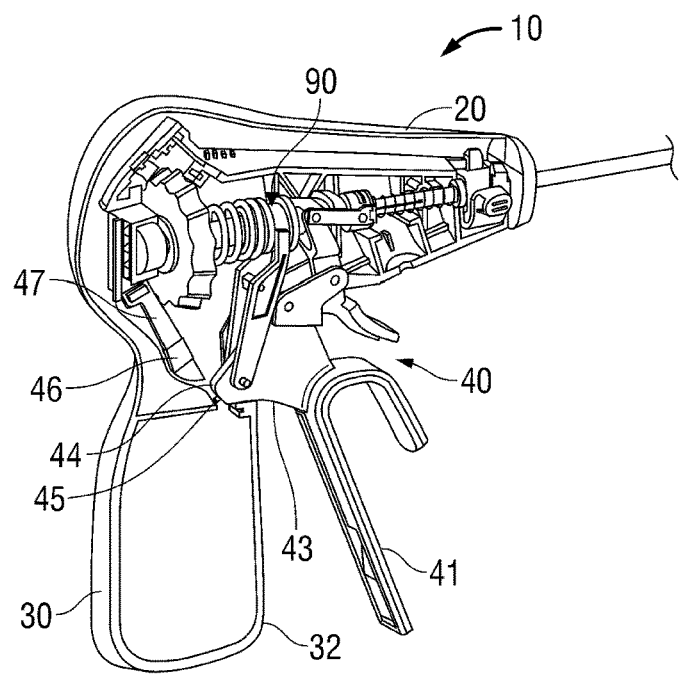
FIG. 2 is a perspective view of a handle assembly of the forceps of FIG. 1A wherein a portion of the housing has been removed to show the internal components therein, the handle assembly including a latch mechanism disposed in an initial position.
Figure 3:
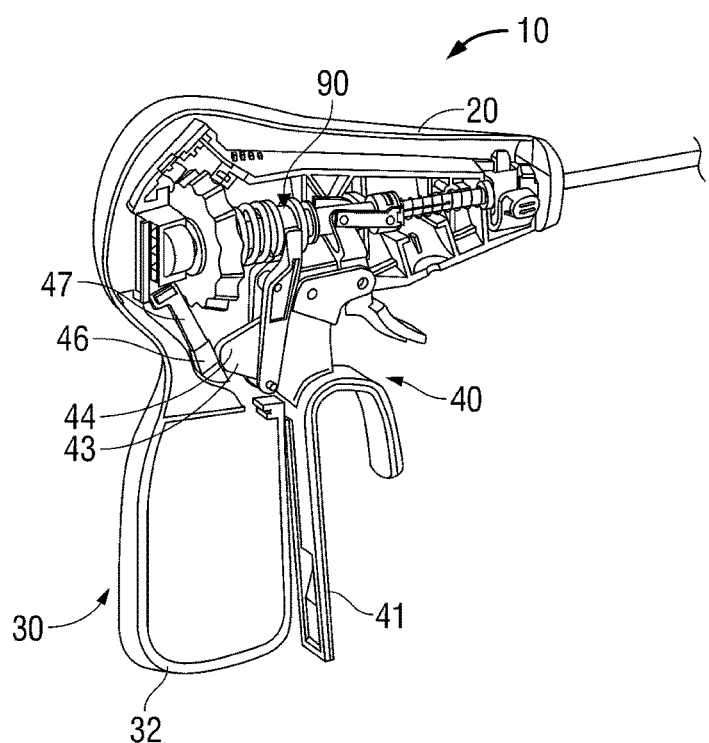
FIG. 3 is a perspective view of the handle assembly of the forceps of FIG. 1A wherein a portion of the housing has been removed to show the internal components therein and wherein the latch mechanism is disposed in an actuated position.

With reference to FIGS. 2 and 3, in conjunction with FIGS. 1A and 1B, battery housing 32 of handle assembly 30 includes mechanical keying features (not shown) configured complementarily to the mechanical keying features associated with housing 20 such that handle assembly 30 may be securely locked in mechanical engagement with housing 20. The battery pack (not shown) is electrically coupled to the generator (not shown), and may also be released from housing 20, e.g., to replace or recharge the battery pack (not shown).

Continuing with reference to FIGS. 2 and 3, one embodiment of a lever latch assembly 40 is shown including a lever 41 pivotably coupled to housing 20 and extending downwardly therefrom. Lever 41 is ultimately connected to drive assembly 90 that, together, mechanically cooperate to impart movement of jaw members 110 and 120 between the spaced-apart position (FIG. 1A) and the approximated position (FIG. 1B). As mentioned above, spatial constraints within housing 20 limit the positioning of lever 41, e.g., such that the generator (not explicitly shown) and other control circuitry (not explicitly shown) may be disposed above drive assembly 90 within housing 20. Further, as will become apparent below, the working components of lever latch assembly 40 are all relatively closely-spaced with respect to one another, thereby providing more area within housing 20 for the generator (not shown) and for engagement of the battery pack (not shown).

Continuing with reference to FIGS. 2 and 3, lever 41 is selectively moveable from an initial position (FIG. 2), wherein lever 41 is spaced-apart from handle assembly 30, to an actuated position (FIG. 3), wherein lever 41 is positioned adjacent to handle assembly 30, to move jaw members 110, 120 from the spaced-apart position (see FIG. 1A) to the approximated position (see FIG. 1B). As will be described below, lever latch assembly 40 is configured to permit movement of lever 41 between the initial position (FIG. 2) and the actuated position (FIG. 3) and for releasably locking lever 41 in the actuated position. Accordingly, lever latch assembly 40 is configured to selectively move jaw members 110, 120 (FIGS. 1A and 1B) between the spaced-apart position and the approximated position and to releasably lock jaw members 110, 120 (FIGS. 1A and 1B) in the approximated position. Further, lever 41 may be biased toward the initial position (FIG. 2), such that jaw members 110, 120 are biased toward the spaced-apart position (FIG. 1A).

Figure 4:
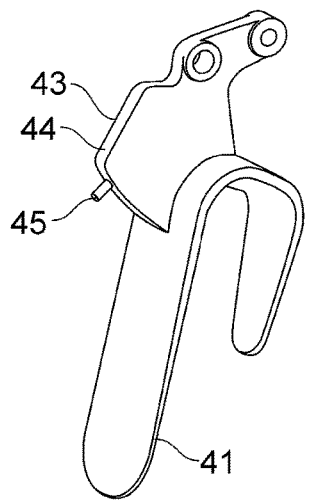
FIG. 4 is an isolated, perspective view of a lever of the latch mechanism of FIGS. 2 and 3.

Turning now to FIG. 4, in conjunction with FIGS. 2-3, lever 41 of lever latch assembly 40 includes a proximally-extending tab 43. Tab 43 extends at least partially into housing 20, e.g., through a slot (not shown) defined therein. More particularly, a proximal tip 44 of tab 43 extends into housing 20 when lever 41 is disposed in the initial position (FIG. 2), while the entire tab 43 (or a substantial portion thereof) extends into housing 20 when lever 41 is moved to the actuated position (FIG. 3). Tab 43 extends into housing 20 above handle assembly 30, as best shown in FIGS. 2 and 3, such that, when the battery pack (not shown) is engaged to housing 20, tab 43 may still be advanced into housing 20 upon movement of lever 41 from the initial position (FIG. 2) to the actuated position (FIG. 3).

Figure 5:
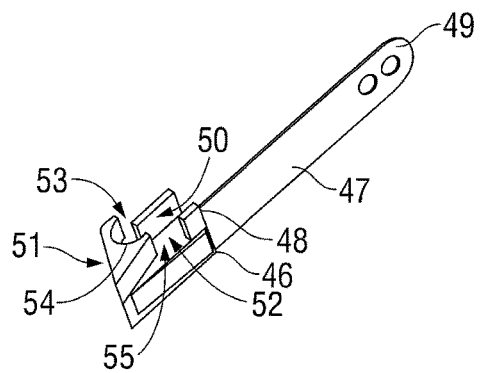
FIG. 5 is an isolated, perspective view of a pin track member and cantilever spring of the latch mechanism of FIGS. 2 and 3.

A pin 45 is integrally formed with, or fixedly engaged to tab 43 of lever 41 and extends proximally therefrom. Pin 45 may be formed from a metal or other rigid material. As tab 43 is advanced into housing 20 upon movement of lever 41 from the initial position to the actuated position, pin 45 is similarly advanced into housing 20 toward pin track member 46 (FIG. 5). In other words pin 45 is translated along an arc upon movement of lever 41 between the initial position and the actuated position. However, since pin 45 is fixedly engaged within lever 41 and since lever 41 is pivotably engaged to housing 20, the transverse position of pin 45 relative to housing 20 is fixed. More specifically, pin 45 is transversely aligned with a neutral axis "N-N" (FIG. 6) defined by cantilever spring 47 throughout movement of lever 41 between the initial position and the actuated position.

Figure 6:
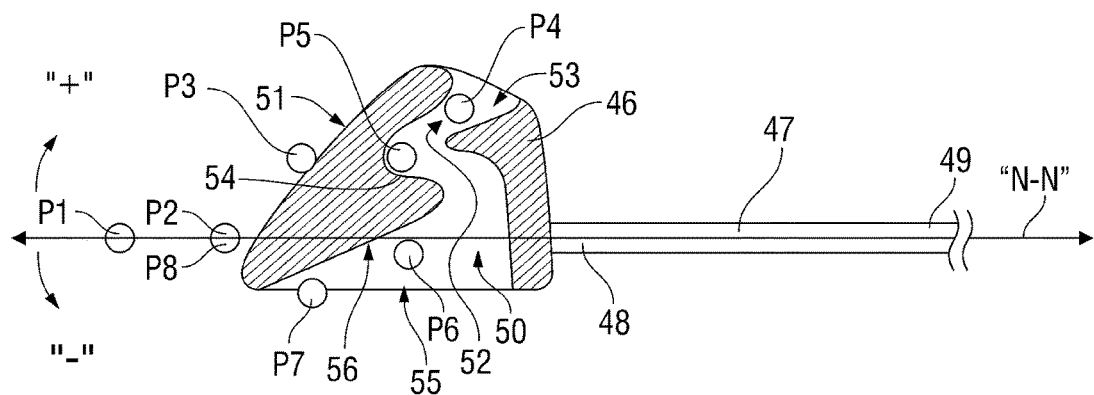
FIG. 6 is a schematic illustration of the use of the latch mechanism of FIGS. 2 and 3.

As best shown in FIG. 5, pin track member 46 defines a track 50 configured to permit translation of pin 45 therealong. Pin track member 46 is engaged, or integrally formed, e.g., insert molded, with a cantilever spring 47 at a first end 48 of cantilever spring 47. Cantilever spring 47 is coupled at a second end 49 thereof to housing 20, e.g., via protrusion-aperture friction fitting, or other suitable engagement. In other words, cantilever spring 47 is fixedly coupled to housing 20 at second end 49 thereof, while first end 48 of cantilever spring 47, having pin track member 46 disposed thereon, is free. At-rest, cantilever spring 47 is biased toward an aligned position defining the neutral axis "N-N" (FIG. 6). However, cantilever spring 47 is capable of being flexed off of the neutral axis "N-N" (FIG. 6) in both a positive direction "+" (FIG. 6) and a negative direction "−" (FIG. 6). As such, upon urging of pin track member 46 and, thus, the free first end 48 of cantilever spring 47 in either direction relative to the fixed second end 49 of cantilever spring 47, cantilever spring 47 is flexed off of the neutral axis "N-N" (FIG. 6) such that pin track member 46 is repositioned relative to the neutral axis "N-N" (FIG. 6). Under the bias of cantilever spring 47 toward an aligned position with respect to the neutral axis "N-N" (FIG. 6), pin track member 46 is likewise biased toward an aligned position with respect to the neutral axis "N-N" (FIG. 6).

Turning now to FIG. 6, in conjunction with FIGS. 2-3, the operation of lever latch assembly 40 will be described. Initially, with lever 41 disposed in the initial position (and, thus, with jaw members 110, 120 disposed in the spaced-apart position (FIG. 1A)), pin 45 extends minimally into housing 20, spaced-apart from pin track member 46. As shown in FIG. 6, this position corresponds to position $P_1$. When it is desired to close jaw members 110, 120 (FIG. 1A), e.g., for grasping tissue therebetween, the surgeon grasps handle assembly 30 and lever 41 and pulls lever 41 proximally toward handle assembly 30, i.e., toward the actuated position. As lever 41 is moved from the initial position toward the actuated position, drive assembly 90 imparts movement of jaw members 110, 120 from the spaced-apart position to the approximated position. At the same time, as lever 41 is pulled proximally, tab 43 is advanced proximally into housing 20 such that pin 45 is translated, in transverse alignment with neutral axis "N-N," toward pin track member 46 to position $P_2$. However, at this point, pin track member 46 remains aligned on the neutral axis "N-N" under the bias of cantilever spring 47.

Upon further movement of lever 41 toward the actuated position, pin 45 is advanced further proximally into housing 20, eventually contacting an outer surface 51 of pin track member 46. With pin 45 transversely fixed with respect to the neutral axis "N-N," pin 45 causes cantilever spring 47 to be flexed and urges pin track member 46 off of the neutral axis "N-N" in a negative direction "−" as pin 45 is translated through position $P_3$. More specifically, the outer surface 51 of pin track member 46 is angled relative to neutral axis "N-N" such that, as lever 41 is pulled further toward the actuated position, pin 45 is slid proximally along outer surface 51 of pin track member 46, urging pin track member 46 off of the neutral axis "N-N."

Once lever 41 has been moved to the actuated position, corresponding to the approximated position of jaw members 110, 120 (FIG. 1B), respectively, of end effector assembly 100, pin 45 has been slid proximally past angled outer surface 51 of pin track member 46 to a position $P_4$ adjacent first end 53 of track channel 52 of pin track member 46. In this position $P_4$, with pin 45 no longer contacting outer surface 51 of pin track member 46, pin 45 no longer urges pin track member 46 off of the neutral axis "N-N." As such, cantilever spring 47 is flexed back toward the aligned position, thereby moving pin track member 46 back toward alignment with the neutral axis "N-N."

When the actuated position of lever 41 has been achieved, such that jaw members 110, 120 (FIG. 1B) are disposed in the approximated position to grasp tissue therebetween, lever 41 is automatically locked in the actuated position to fix jaw members 110, 120 (FIG. 1B) in the approximated position. More particularly, once pin 45 is positioned adjacent first end 53 of track channel 52, cantilever spring 47 biases pin track member 46 back toward the neutral axis "N-N" such that pin 45 is translated along track channel 52 from position $P_4$ at the first end 53 of track channel 52 to position $P_5$ at the saddle portion 54 of track channel 52. Even if lever 41 is released at this point, pin 45 is retained in position within saddle portion 54 of track channel 52 of pin track member 46. Specifically, pin track member 46 inhibits distal translation of pin 45 and, thus lever 41, thereby maintaining jaw members 110, 120 (FIG. 1B) in the approximated position. Further, with pin 45 disposed in position $P_5$, i.e., with pin 45 disposed within saddle portion 54 of track channel 52 of pin track member 46, pin track member 46 is inhibited from returned into alignment with neutral axis "N-N."

Pin track member 46 may include one or more feedback features (not shown) for providing tactile and/or audible feedback notifying the surgeon that lever 41 has been translated to the actuated position. For example, saddle portion 54 may be configured to provide an audible or tactile response when pin 45 is translated into saddle portion 54, e.g., when pin 45 is moved to position $P_5$. Such a feature indicates to the surgeon that lever latch assembly 40 is in the locked position and that lever 41 may be released to lock jaw members 110, 120 in the approximated position.

With lever latch assembly 40 maintaining lever 41 in the actuated position and, thus, maintaining jaw members 110, 120 (FIG. 1B) in the approximated position with tissue grasped therebetween, electrosurgical energy may be supplied to sealing surfaces 112, 122 of jaw members 110, 120, respectively, to effect a tissue seal (see FIG. 1B). Thereafter, trigger 82 may be actuated to advance the blade (not shown) between jaw members 110, 120 to cut tissue along the previously formed tissue seal. Finally, lever latch assembly 40 may be unlatched, as described in further detail below, allowing lever 41 to return to the initial position and allowing jaw members 110, 120 (FIGS. 1A and 1B) to return to the spaced-apart position to release tissue such that forceps 10 may be removed from the surgical site.

In order to unlock lever latch assembly 40, lever 41 is moved further proximally from the actuated position a sufficient distance to dislodge pin 45 from saddle portion 54 of track channel 52 of pin track member 46. In other words, lever 41 is moved proximally such that pin 45 is no longer retained within saddle portion 54. Track channel 52 is configured such that, once pin 45 is removed from saddle portion 54, pin 45 enters open second end 55 of track channel 52. Once pin 45 is moved into the open second end 55 of track channel 52, e.g., once pin 45 is moved to position $P_6$, pin 45 no longer inhibits pin track member 46 from returning under the bias of cantilever spring 47 to the aligned position with respect to neutral axis "N-N." As such, cantilever spring 47 is returned to the at-rest position, thereby returning pin track member 46 into alignment with neutral axis "N-N."

At this point, with pin 45 in position $P_6$, the surgeon may release lever 41. Similarly as discussed above, pin track member 46 may include feedback features (not shown) for providing a tactile or audible indication to the surgeon that pin 45 has been removed from saddle portion 54 of track channel 52 and, thus, that lever 41 may be released allowing jaw members 110, 120 (FIGS. 1A and 1B) to return to the spaced-apart position.

Upon release of lever 41 by the surgeon, lever 41 is returned back to the initial position. As such, pin 45 is translated distally relative to pin track member 46 and housing 20. More particularly, pin 45 is translated distally from position $P_6$ along inner surface 56 of pin track member 46. Inner surface 56 of pin track member 46 is angled such that, as pin 45 is translated therealong to position $P_7$, cantilever spring 47 is flexed to permit pin track member 46 to be repositioned off of the neutral axis "N-N" in a positive direction "+." Upon further distal translation of pin 45 to position $P_8$, pin 45 exits second end 55 of track channel 52 of pin track member 46, allowing pin track member 46 to return under the bias of cantilever spring 47 back into alignment with the neutral axis "N-N." Thereafter, lever is further returned, e.g., under the bias, back to the initial position corresponding to position $P_1$ of pin 45 and corresponding to the spaced-apart position of jaw members 110, 120 of end effector assembly 100 (FIGS. 1A and 1B).

Turning now to FIGS. 7-9, another embodiment of a lever latch assembly 60 is shown configured for use with a surgical instrument, e.g., forceps 10. Similar to lever latch assembly 40 discussed above (see FIGS. 2-6), lever latch assembly 60 includes a lever 61 pivotably coupled to housing 20 and extending downwardly therefrom. Lever 61 is ultimately connected to drive assembly 90 that, together, mechanically cooperate to impart movement of jaw members 110 and 120 between the spaced-apart position (FIG. 1A) and the approximated position (FIG. 1B). More particularly, lever 61 is selectively moveable from an initial position, wherein lever 61 is spaced-apart from handle assembly 30, to an actuated position, wherein lever 61 is positioned adjacent to handle assembly 30, to move jaw members 110, 120 from the spaced-apart position (see FIG. 1A) to the approximated position (see FIG. 1B).

With continued reference to FIGS. 7-9, lever latch assembly 60 is similar to lever latch assembly 40 in that lever latch assembly 60 is configured to permit movement of lever 61 between the initial position and the actuated position and for relesably locking lever 61 in the actuated position. Accordingly, lever latch assembly 60 is configured to selectively move jaw members 110, 120 between the spaced-apart position (FIG. 1A) and the approximated position (FIG. 1B) and to releasably lock jaw members 110, 120 in the approximated position (FIG. 1B). Further, lever 61 may be biased toward the initial position, such that jaw members 110, 120 are biased toward the spaced-apart position (FIG. 1A).

As best shown in FIG. 9, lever 61 of lever latch assembly 60 includes a pair of flanges 63 extending upwardly therefrom. Flanges 63 extend into housing 20 to couple lever 61 to housing 20. A crossbar 64 extends between flanges 63 in a generally perpendicular orientation with respect to flanges 63. A cantilever spring 65 is fixedly engaged at a first end 67 thereof to crossbar 64 and includes a pin 66 integrally formed with, or otherwise engaged to free second end 68 of cantilever spring 65. Cantilever spring 65 extends downwardly and proximally from crossbar 64 of flanges 63 of lever 61 such that pin 66 extends generally toward housing 20. More specifically, when lever 61 is disposed in the initial position, pin 66 is spaced-apart from housing 20. On the other hand, when lever 61 is moved to the actuated position, pin 66 is positioned adjacent housing 20. Further, cantilever spring 65 is positioned off-center on crossbar 64, i.e., cantilever spring 65 is positioned asymmetrically between flanges 63 of lever 61. At-rest, cantilever spring 65 is biased toward an aligned position defining the neutral axis "N-N" (FIGS. 10 and 11). However, cantilever spring 65, similar to cantilever spring 65, is capable of being flexed off of the neutral axis "N-N" (FIGS. 10 and 11) in both a position direction "+" and a negative direction "−" to thereby reposition pin 66 off of the neutral axis "N-N" (FIGS. 10 and 11).

Referring to FIGS. 7-11, lever latch assembly 60 also includes a pin track member 69 defining a track 70 configured to permit translation of pin 66 therealong. Pin track member 69 is engaged to, or integrally formed with housing 20 in a generally distal-facing orientation and is positioned to at least partially intersect the neutral axis "N-N." As such, upon movement of lever 61 from the initial position to the actuated position, pin 66 is translated along an arc toward housing 20 and, thus, toward pin track member 69, eventually engaging pin track member 69. As will be described in greater detail below, with pin track member 69 fixedly engaged to housing 20, and with pin 66 engaged to lever 61 via cantilever spring 65, movement of lever 61 between the initial position and the actuated position causes pin track member 69 to urge the free second end 68 of cantilever spring 65 off of the neutral axis "N-N" such that pin 66 is repositioned relative to the neutral axis "N-N" to releasably lock lever 61 in the actuated position.

The operation of lever latch assembly 60 will now be described. Initially, with lever 61 disposed in the initial position (and, thus, with jaw members 110, 120 disposed in the spaced-apart position (FIG. 1A)), pin 66 is spaced-apart from pin track member 69 and, thus, cantilever spring 65 is aligned on neutral axis "N-N." As shown in FIG. 6, this position corresponds to position $P_1'$. When it is desired to close jaw members 110, 120 (FIGS. 1A-1B), e.g., for grasping tissue therebetween, the surgeon grasps handle assembly 30 and lever 61 and pulls lever 61 proximally toward handle assembly 30, i.e., toward the actuated position. As lever 61 is moved from the initial position toward the actuated position, drive assembly 90 imparts movement of jaw members 110, 120 from the spaced-apart position to the approximated position (FIG. 1B). At the same time, as lever 61 is pulled proximally, pin 66 is advanced proximally toward housing 20 such that pin 66 is translated toward pin track member 69, represented by position $P_2'$. However, at this point, pin 66 is still spaced from pin track member 69 and, thus, remains aligned on the neutral axis "N-N" under the bias of cantilever spring 65.

Upon further movement of lever 61 toward the actuated position, pin 66 is advanced further proximally toward housing 20, eventually contacting an outer surface 71 of pin track member 69. Due to the angled configuration of outer surface 71 of pin track member 69 relative to the neutral axis "N-N," and with pin track member 69 transversely fixed with respect to the neutral axis "N-N," cantilever spring 65 is flexed and pin 66 is urged of the neutral axis "N-N" in a negative direction "−" as pin 66 is translated through position $P_3'$ and along outer surface 71.

Once lever 61 has been moved to the actuated position, corresponding to the approximated position of jaw members 110, 120, respectively, of end effector assembly 100 (FIGS. 1A and 1B), pin 66 has been slid proximally past angled outer surface 71 of pin track member 69 to a position $P_4'$ adjacent first end 72 of track channel 74 of pin track member 69. In this position $P_4'$, with pin 66 no longer contacting outer surface 71 of pin track member 69, pin track member 69 no longer urges pin 66 off of the neutral axis "N-N." As such, cantilever spring 65 is flexed back toward the aligned position, thereby moving pin 66 back toward alignment with the neutral axis "N-N."

When lever is moved to the actuated position and is subsequently released, lever latch assembly 60 releasably locks lever 61 in the actuated position to fix jaw members 110, 120 in the approximated position (see FIG. 1B). More particularly, once pin 66 is positioned adjacent first end 72 of track channel 74, cantilever spring 65 biases pin 66 back toward the neutral axis "N-N" such that pin 66 is translated along track channel 74 from position $P_4'$ at the first end 72 of track channel 74 to position P$_5$' at the saddle portion 75 of track channel 74. In this position, pin track member 69 inhibits distal translation of pin 66 and, thus lever 61, thereby maintaining jaw members 110, 120 in the approximated position. As in the previous embodiment, pin 66 and/or pin track member 69 may include one or more feedback features (not shown) for providing tactile and/or audible feedback notifying the surgeon that lever 61 has been translated to the actuated position.

With lever latch assembly 60 maintaining lever 61 in the actuated position and, thus, maintaining jaw members 110, 120 (FIG. 1B) in the approximated position with tissue grasped therebetween, electrosurgical energy may be supplied to sealing surfaces 112, 122 of jaw members 110, 120, respectively, to effect a tissue seal (see FIG. 1B). Thereafter, trigger 82 may be actuated to advance the blade (not shown) between jaw members 110, 120 (FIG. 1B) to cut tissue along the previously formed tissue seal. Finally, lever latch assembly 60 may be unlatched, as will be described in greater detail below, allowing lever 61 to return to the initial position and allowing jaw members 110, 120 (FIGS. 1A and 1B) to return to the spaced-apart position to release tissue such that forceps 10 may be removed from the surgical site.

In order to unlock lever latch assembly 60, lever 61 is moved further proximally from the actuated position a sufficient distance to dislodge pin 66 from saddle portion 75 of track channel 74 of pin track member 69. In other words, lever 61 is moved proximally such that pin 66 is no longer retained within saddle portion 75. Track channel 74 is configured such that, once pin 66 is removed from saddle portion 75, pin 66 enters open second end 73 of track channel 74. Once pin 66 is moved into the open second end 73 of track channel 74, e.g., once pin 66 is moved to position P$_6$', pin track member 69 no longer inhibits pin 66 from returning under the bias of cantilever spring 65 to the aligned position with respect to neutral axis "N-N." As such, cantilever spring 65 is returned to the at-rest position, thereby returning pin 66 into alignment with neutral axis "N-N." At this point, with pin 66 in position P$_6$', the surgeon may release lever 61, allowing jaw members 110, 120 to return to the spaced-apart position (see FIG. 1A). Upon release of lever 61 by the surgeon, lever 61 is returned back to the initial position. As such, pin 66 is translated distally relative to pin track member 69 and housing 20. More particularly, pin 66 is translated distally from position P$_6$' along inner surface 76 of pin track member 69. Inner surface 76 of pin track member 69 is angled such that, as pin 66 is translated therealong to position P$_7$', cantilever spring 65 is flexed to permit pin 66 to be repositioned off of the neutral axis "N-N" in a positive direction "+." Upon further distal translation of pin 66 to position P$_8$', pin 66 exits second end 73 of track channel 74 of pin track member 69, allowing pin 66 to return under the bias of cantilever spring 65 back into alignment with the neutral axis "N-N." Thereafter, lever 61 is further returned, e.g., under the bias, back to the initial position corresponding to position P$_1$' of pin 66 and corresponding to the spaced-apart position of jaw members 110, 120 of end effector assembly 100 (FIG. 1A).

Referring to FIGS. 12-14C, a blade 1200 configured for use with forceps 10 (FIG. 1A), or any other suitable surgical instrument, generally includes a blade 1201 engaged to a blade shaft 1203 having at least one pin hole 1205 defined therein. Blade 1200 is configured for slidable translation within shaft 1307 (similar to shaft 12 of forceps 10 (FIG. 1A)) such that blade 1200 may slide through and relative to shaft 1307 between a retracted position and a deployed position, wherein blade 1201 extends at least partially between jaw members 1310, 1320 of end effector assembly 1301 (similar to end effector assembly 100 of forceps 10 (FIG. 1A)).

Figure 14A:
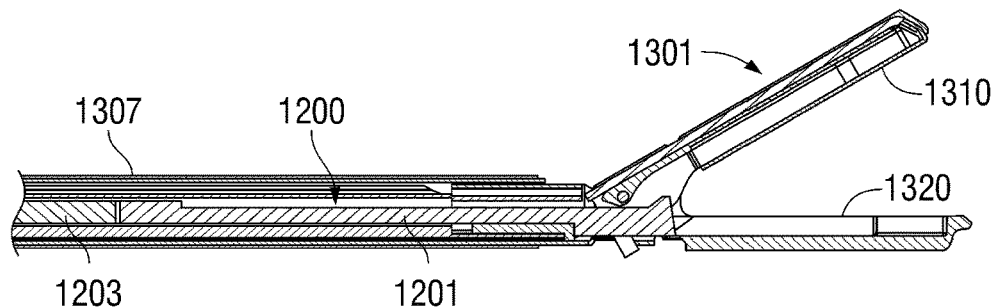
FIG. 14A is a cross-sectional view of the end effector assembly of FIG. 13 in an open position with the blade in a retracted position.
Figure 14B:
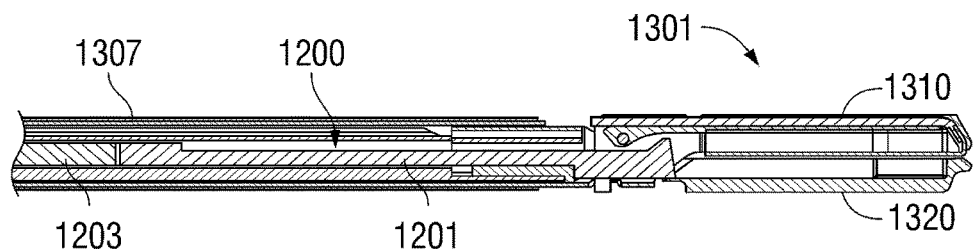
FIG. 14B is a cross-sectional view of the end effector assembly of FIG. 13 in a closed position with the blade in the retracted position.
Figure 14C:
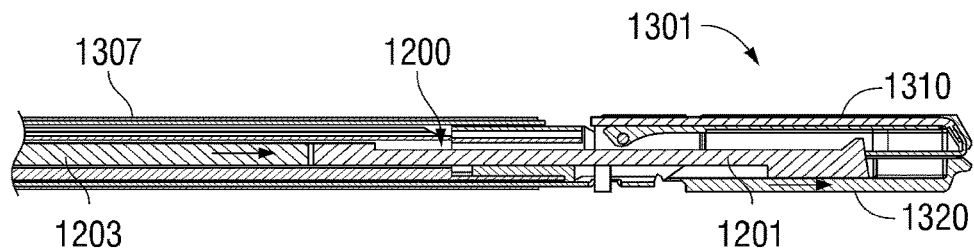
FIG. 14C is a cross-sectional view of the end effector assembly of FIG. 13 in a closed position with the blade in a deployed position.

Referring to FIGS. 14A, 14B and 14C, shaft 1307 and end effector assembly 1301 are shown incorporating blade 1200 therein. In FIG. 14A, jaw members 1310, 1320 are disposed in an open position and blade 1201 is disposed in a retracted position. In FIG. 14B, jaw members 1310, 1320 are disposed in a closed position, while blade 1201 remains disposed in the retracted position. In FIG. 14C, jaw members 1310, 1320 are in the closed position and the blade 1201 has been deployed to extend at least partially between jaw members 1310, 1320.

Turning now to FIGS. 15A, 15B, 15C, and 15D, in conjunction with FIGS. 12, 13 and 14A-14C, a handle and trigger assembly 1500 is shown configured to operate blade 1200 and end effector assembly 1301. Handle and trigger assembly 1500 includes a trigger member 1502 that is pivotably coupled to the housing of the instrument (e.g., housing 20 of forceps 10 (FIG. 1A)) at a first pivot 1505. The trigger member 1502 is operably coupled to a blade deployment member 1510 at a second pivot 1511. More specifically, second pivot 1511 couples trigger member 1502 to blade deployment member 1510 at one end of blade deployment member 1510, while engagement pin 1513 couples the other end of blade deployment member 1510 to blade shaft 1203 of blade 1200 via engagement of engagement pin 1513 through a slot 1305 defined within shaft 1307 and into engagement with pinhole 1205 defined within blade shaft 1203. The slot 1305 defined within shaft 1307 allows translation of engagement pin 1513 so that blade 1200 easily transitions within shaft 1200, e.g., between the retracted and deployed positions (FIGS. 14B and 14C, respectively). Any of the pivots may be any functional mechanical interface suitable for the desired purpose including, but not limited to, a rotatable connection, a slidable connection, a cam-follower, etc.

In operation, as the trigger member 1502 is pulled proximally, from an un-actuated position towards an actuated position, trigger member 1502 is pivoted about first pivot 1505 and blade deployment assembly member 1510 is translated distally such that engagement pin 1513, which, as mentioned above, is engaged to blade shaft 1203 of blade 1200 via pin hole 1205, is slid along slot 1305 allowing the blade 1200 to slidably move within shaft 1307, ultimately to deploy blade 1201 between jaw members 1310, 1320 of end effector assembly 1301, e.g., to move blade 1201 between the retracted and deployed positions (FIGS. 14B and 14C, respectively). Movement of the trigger member 1502 about first pivot 1505 in the other direction, e.g., back towards the un-actuated position, retracts blade 1200. A spring 1550 disposed about shaft 1307 may function to bias trigger member 1502 distally, such that, upon release of trigger member 1502, trigger member 1502 is returned distally to the un-actuated position such that blade 1201 is returned to the retracted position.

Handle and trigger assembly 1500 further includes a lever member 1544, at least a portion of which is disposed inside the housing of the instrument (e.g., housing 20 of forceps 10 (FIG. 1A)) and operably coupled to the housing via a third pivot. In an embodiment, pivot 1505 functions as both the first and third pivots, e.g., the pivot 1505 for both lever member 1544 and trigger member 1502 as is shown in FIGS. 15A-15D. Lever member 1544 is configured to move between a first or initial position and a second or compressed position to open and close jaw members 1310, 1320 of end effector assembly 1301 in a similar manner as described above with reference to lever 40 and jaw members 110, 120 (see FIGS. 1A-11).

Handle and trigger assembly 1500 further includes driving member 1501 operably coupled to a drive assembly 1590 at a driving end 1507. The driving member 1501 may be operably connected to the housing (not shown) via at a point, e.g. a fourth pivot 1508. Driving member 1501 is coupled to end effector assembly 1301 via drive assembly 1590 such that movement of driving member 1501 effects longitudinal translation of drive assembly 1590 which, in turn, effects movement of jaw members 1310, 1320 of end effector assembly 1301 between the open and closed positions. Driving end 1507 of driving member 1501 may be operably connected to drive assembly 1590 via engagement of driving end 1507 within mandrel 1592 of drive assembly 1590. Other suitable connections may also be used.

Driving member 1501 is coupled to lever member 1544 such that, upon movement of lever member 1544 from the initial position to the compressed position, driving member 1501 is pivoted about fourth pivot 1508 to urge drive assembly 1590 to translate proximally, thereby moving jaw members 1310, 1320 of end effector assembly 1301 from the open position to the closed position to grasp tissue therebetween. Moving lever member 1544 from the compressed position back to the initial position returns jaw members 1310, 1320 of end effector assembly 1301 to the open position. A spring 1560 disposed about drive assembly 1590 may function to bias drive assembly 1590 distally such that, upon release of lever member 1544, lever member 1544 is returned to the initial position and jaw members 1310, 1320 are returned to the open position.

Handle and trigger assembly 1500 further includes a trigger safety member 1503 that is operably coupled between lever member 1544, trigger member 1502, and driving member 1501. More specifically, trigger safety member 1503 is coupled to lever member 1544 via a fifth or trigger pivot 1506 and to driving member 1501 at a different point, e.g. via a sixth pivot 1504. Trigger safety member 1503 includes a first portion 1503a extending distally from fifth pivot 1506 and a second portion 1503b extending proximally from fifth pivot 1506 and coupled to driving member 1501 via sixth pivot 1504.

Figure 15A:
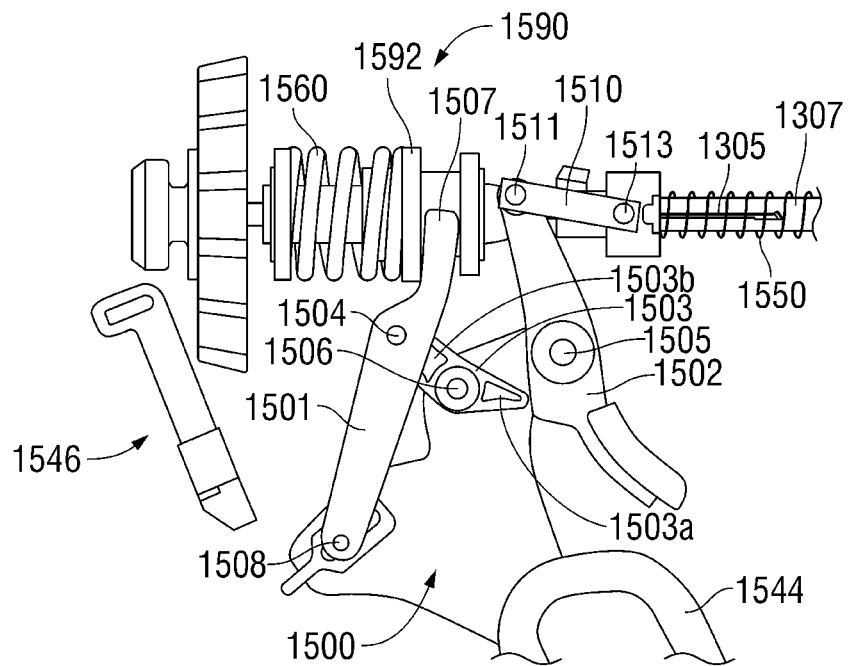
FIG. 15A is a side view of a handle and trigger assembly provided in accordance with an aspect of the present disclosure, wherein the lever member is in an initial position and the trigger is locked-out.

When the lever member 1544 is in the initial position, as shown in FIG. 15A, in conjunction with FIGS. 12, 13 and 14A-14C, trigger safety member 1503 is oriented such that first portion 1503a of safety member 1503 blocks, or prevents trigger member 1502 from being actuated. More specifically, first portion 1503a of safety member 1503 intercepts the path of trigger member 1502 below first pivot 1505 to prevent pivoting of trigger member 1502 to deploy blade 1201. This position of safety member 1503 corresponds to a locked state of handle and trigger assembly 1500. As can be appreciated, in this locked state, safety member 1503 inhibits deployment of blade 1201 when the lever 1544 is not being compressed. Generally, when the lever 1544 is uncompressed, the jaw members 1310, 1320 are disposed in the open position, and when the lever 1544 is compressed, the jaw members 1310, 1320 are in the closed position. However, the jaw members 1310, 1320 may be held in a substantially open position by thick tissue even when the lever 1544 is compressed, in which case the blade 1201 may still be deployed as the safety member 1503 is rotated out of the path of the trigger member 1502 due to the position of the lever 1544.

Figure 15B:
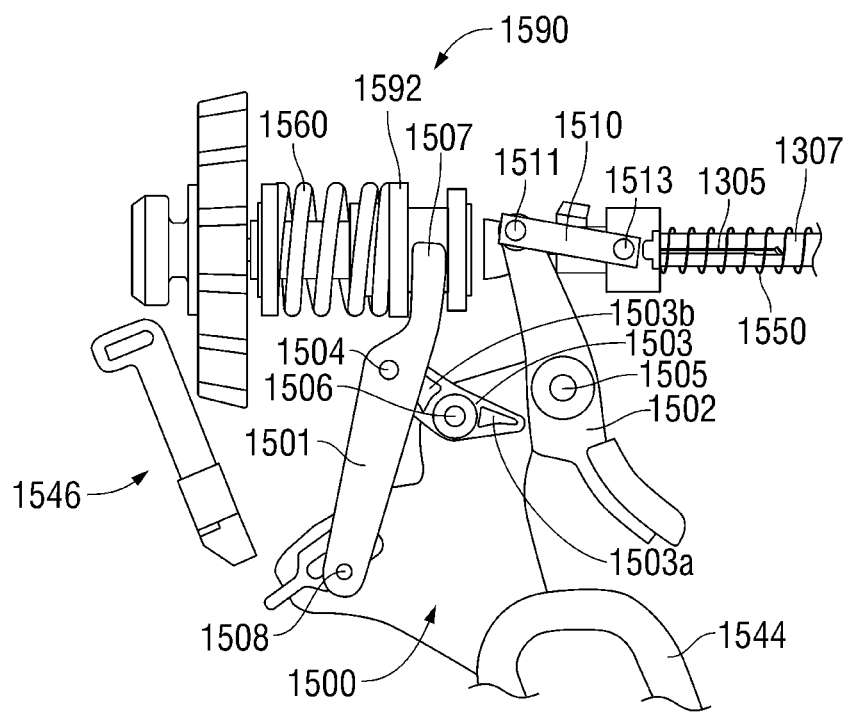
FIG. 15B is a side view of the handle and trigger assembly of FIG. 15A where the lever member is in a transitional state between the initial position and a compressed position.

As shown in FIG. 15B, in conjunction with FIGS. 12, 13 and 14A-14C, as lever 1544 is moved from the initial position towards the compressed position to close jaw members 1310, 1320, safety member 1503 begins to rotate about pivot 1506 out of the path of trigger member 1502 so as to no longer block, or inhibit deployment of blade 1201. The position of the lever 1544 that is required to allow safety member 1503 to no longer block the trigger member 1502 may be selectable as a design feature as desired. For example, the safety member 1503 may block the trigger member 1502 until the lever 1544 is completely compressed. Alternatively, the safety member 1503 may allow the trigger member 1502 to be operated when the lever is at any desired position between the initial position and the compressed position.

Figure 15C:
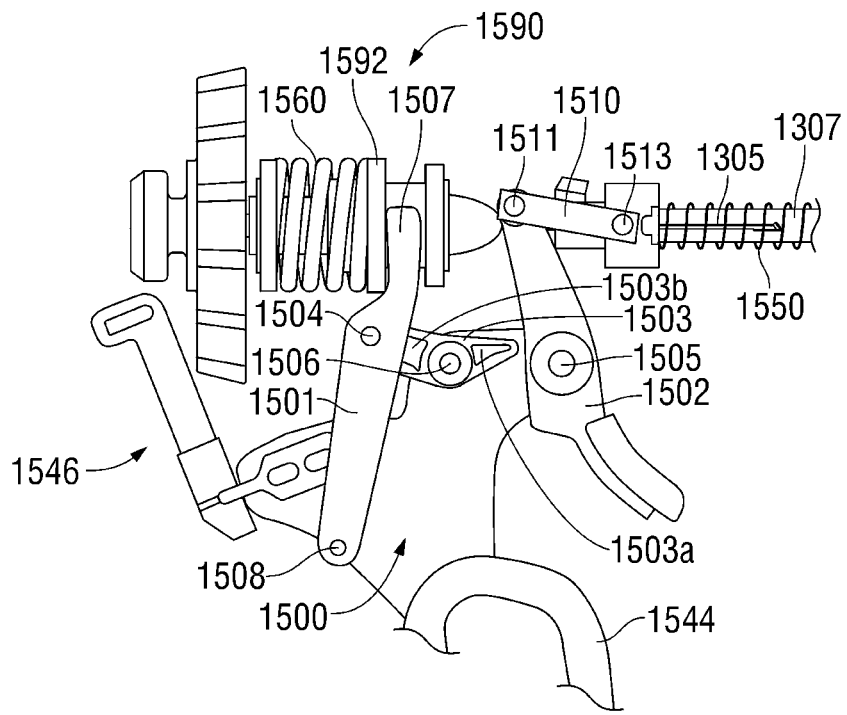
FIG. 15C is a side view of the handle and trigger assembly of FIG. 15A, wherein the lever member is in the compressed position and the trigger is unlocked.

Turning to FIG. 15C, in conjunction with FIGS. 12, 13 and 14A-14C, once lever member 1544 reaches the compressed position, trigger safety member 1503 has already rotated out of the path of trigger member 1502 such that trigger member 1502 may be actuated by the user, e.g., rotated proximally about pivot 1505, to deploy blade 1201 between jaw members 1310, 1320 to cut tissue grasped therebetween. More specifically, as shown in FIG. 15C, with lever member 1544 in the compressed position, first portion 1503a of safety member 1503 no longer intercepts the path of trigger member 1502, but, rather, is rotated such that first portion 1503a is disposed above pivot 1505, no longer interfering with the range of motion of trigger member 1502. This position of safety member 1503 corresponds to an unlocked state of handle and trigger assembly 1500.

Figure 15D:
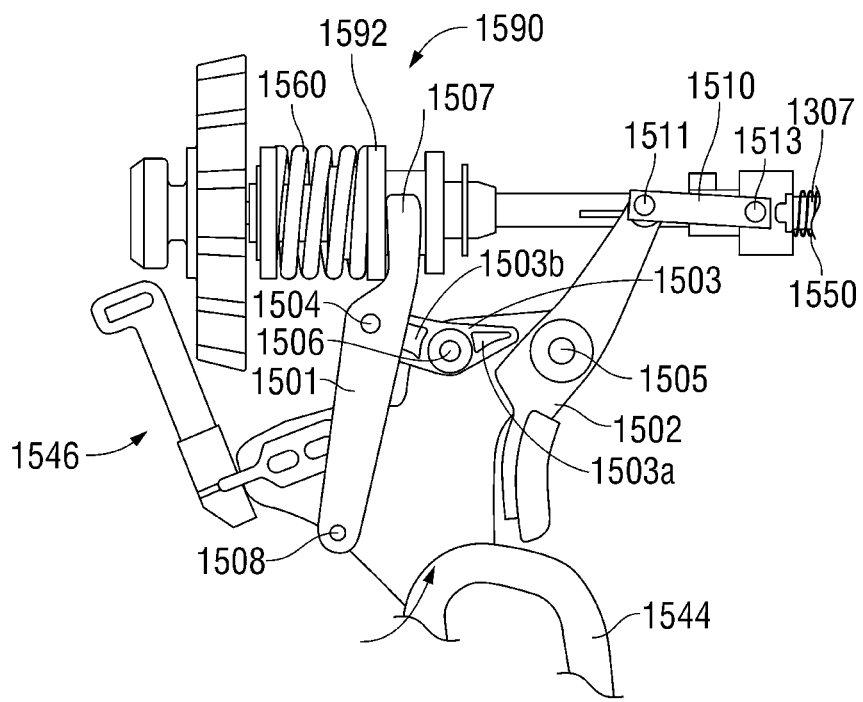
FIG. 15D is a side view of the handle and trigger assembly of FIG. 15A, wherein the lever is in the compressed position and the trigger has been activated.

Turning to FIG. 15D, in conjunction with FIGS. 12, 13 and 14A-14C, with lever member 1544 in the compressed position, and, thus, with handle and trigger assembly 1500 is in the unlocked state, trigger member 1502 may be actuated to deploy blade 1201 between jaw members 1310, 1320 of end effector assembly 1301 to cut tissue grasped therebetween.

Handle and trigger assembly 1500 may further include a latch mechanism 1546, similar to any of the latch mechanisms described above (see FIGS. 1-11), or any other suitable latch mechanism. Latch mechanism 1546 is configured to releasably retain lever member 1544 in the compressed position, thereby maintaining jaw members 1310, 1320 in the closed position.

Upon unlatching lever member 1544 from latch mechanism 1546 and returning lever member 1544 towards the initial position (or, simply upon return of lever member 1544, in instances where latching is not provided or used), safety member 1503 is rotated and translated back towards the locked state. Such a feature is particularly useful in situations where trigger member 1502 is stuck in the deployed position, e.g., where trigger member 1502 does not return under bias of spring 1550 after being released. More specifically, as safety member 1503 is rotated and translated back towards the locked state, first portion 1503a contacts trigger member 1502 (if trigger member 1502 has not already been returned under bias to the initial position) and urges trigger member 1502 back towards its initial position, thereby returning blade 1201 to the retracted position. In other words, not only does safety member 1503 provide a "safety lockout" that inhibits deployment of blade 1201 when jaw members 1310, 1320 are in the open position, but safety member 1503 also provides a "kickback" feature that returns blade 1201 to the retracted position as jaw members 1310, 1320 are returned to the open position.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed:

1. A surgical instrument, comprising:
   an end effector assembly having an open position and a closed position;
   a lever movable between a first position and a second position;
   a driving member operably coupled to the end effector assembly and the lever such that movement of the lever between the first position and the second position moves the end effector assembly between the open position and the closed position;
   a blade operably coupled to the end effector assembly and movable between a retracted position and a deployed position, wherein the end effector is movable between the open position and the closed position independently of movement of the blade;
   a trigger member operably coupled to the blade and movable along an actuation path to move the blade between the retracted position and the deployed position; and
   a trigger safety member directly coupled to the lever about a first pivot, directly coupled to the driving member about a second pivot, extending continuously and directly between the first and second pivots, and configured such that, when the lever is disposed in the first position, the trigger safety member is disposed in the actuation path to block actuation of the trigger member, and when the lever is disposed in the second position, the trigger safety member is displaced from the actuation path to permit actuation of the trigger member.

2. The surgical instrument of claim 1, wherein the trigger safety member rotates relative to the lever about the first pivot as a function of movement of the lever to block/unblock the trigger member.

3. The surgical instrument of claim 1, further comprising a housing enclosing at least a portion of the lever, the trigger member, and the trigger safety member.

4. The surgical instrument of claim 3, wherein the lever and the trigger member are operably coupled to the housing at different pivots.

5. The surgical instrument of claim 3, wherein the lever and the trigger member are operably coupled to the housing at a common pivot.

6. The surgical instrument of claim 1, wherein the end effector assembly includes first and second jaw members, at least one of the jaw members movable relative to the other between the open position and the closed position.

7. The surgical instrument of claim 1, further comprising at least one blade deployment member operably coupled between the blade and the trigger member.

8. The surgical instrument of claim 1, further comprising a latch mechanism configured to releasably secure the lever in the second position.

9. The surgical instrument of claim 1, wherein, when the lever is returned from the second position to the first position, the trigger safety member forcibly urges the trigger along the actuation path back to an un-actuated position.

10. A surgical instrument, comprising:
    an end effector assembly movable between an open position and a closed position;
    a lever movable between an initial position and a compressed position;
    a driving member operably coupled between the lever and the end effector assembly such that movement of the lever between the initial position and the compressed position translates the driving member between a first position and a second position to move the end effector assembly between the open position and the closed position;
    a blade operably coupled to the end effector assembly and movable between a retracted position and a deployed position, wherein the end effector is movable between the open position and the closed position independently of movement of the blade;
    a trigger operably coupled to the blade and movable from an un-actuated position to an actuated position along an actuation path to move the blade from the retracted position to the deployed position; and
    a trigger safety member directly coupled to the drive member and configured such that, when the lever is disposed in the first position, the trigger safety member is disposed in the actuation path to block actuation of the trigger from the un-actuated position to the actuated position, when the lever is disposed in the second position, the trigger safety member is displaced from the actuation path to permit movement of the trigger from the un-actuated position to the actuated position, and when the lever is returned from the second position to the first position, the trigger safety member directly contacts and forcibly urges the trigger along the actuation path back to the un-actuated position.

11. The surgical instrument of claim 10, wherein the driving member is biased towards the first position and wherein, when the lever is returned from the second position to the first position, the trigger safety member forcibly urges the trigger along the actuation path back to the un-actuated position under the bias of the driving member.

12. The surgical instrument of claim 10, wherein the trigger safety member rotates relative to the driving member as a function of movement of the lever to block/unblock the trigger.

13. The surgical instrument of claim 10, wherein the trigger safety member is also directly coupled to the lever.

14. The surgical instrument of claim 13, wherein the trigger safety member is directly coupled to the lever about a first pivot and directly coupled to the driving member about a second pivot.

15. The surgical instrument of claim 10, further comprising a housing enclosing at least a portion of the lever, the trigger, and the trigger safety member.

16. The surgical instrument of claim 15, wherein the lever and the trigger are operably coupled to the housing at different pivots.

17. The surgical instrument of claim 15, wherein the lever and the trigger are operably coupled to the housing at a common pivot.

18. The surgical instrument of claim 10, wherein the end effector assembly includes first and second jaw members, at least one of the jaw members movable relative to the other between the open position and the closed position.

19. The surgical instrument of claim 10, further comprising at least one blade deployment member operably coupled between the blade and the trigger.

20. The surgical instrument of claim 10, further comprising a latch mechanism configured to releasably secure the lever in the compressed position.

\* \* \* \* \*